United States Patent
Lerchen et al.

(10) Patent No.: US 8,362,015 B2
(45) Date of Patent: Jan. 29, 2013

(54) AMINOACYL PRODRUG DERIVATIVES AND MEDICAMENTS FOR TREATMENT OF THROMBOEMBOLIC DISORDERS

(75) Inventors: Hans-Georg Lerchen, Leverkusen (DE); Ursula Krenz, Leichlingen (DE); Karl-Heinz Schlemmer, Wuppertal (DE); Elisabeth Perzborn, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 478 days.

(21) Appl. No.: 12/438,097

(22) PCT Filed: Aug. 23, 2007

(86) PCT No.: PCT/EP2007/007408
§ 371 (c)(1),
(2), (4) Date: May 25, 2010

(87) PCT Pub. No.: WO2008/022786
PCT Pub. Date: Feb. 28, 2008

(65) Prior Publication Data
US 2010/0292230 A1  Nov. 18, 2010

(30) Foreign Application Priority Data
Aug. 24, 2006 (DE) .......................... 10 2006 039 589

(51) Int. Cl.
A61K 31/535 (2006.01)
C07D 413/14 (2006.01)
(52) U.S. Cl. .................................... 514/236.8; 544/137
(58) Field of Classification Search .................. 544/137; 514/236.8
See application file for complete search history.

(56) References Cited

U.S. PATENT DOCUMENTS

| | | | |
|---|---|---|---|
| 7,157,456 B2 | 1/2007 | Straub et al. | |
| 7,351,823 B2 | 4/2008 | Berwe et al. | |
| 7,767,702 B2 | 8/2010 | Straub et al. | |
| 8,101,601 B2 * | 1/2012 | Lerchen et al. | 514/230.8 |
| 8,153,670 B2 | 4/2012 | Zhu et al. | |
| 8,198,267 B2 | 6/2012 | Allerheiligen et al. | |
| 2007/0026065 A1 | 2/2007 | Benke et al. | |
| 2008/0026057 A1 | 1/2008 | Benke | |
| 2008/0306070 A1 | 12/2008 | Perzborn et al. | |
| 2010/0029651 A1 | 2/2010 | Härter et al. | |
| 2010/0184740 A1 | 7/2010 | Allerheiligen et al. | |
| 2010/0261759 A1 | 10/2010 | Allerheiligen et al. | |

FOREIGN PATENT DOCUMENTS

| | | |
|---|---|---|
| WO | WO-01/00622 | 1/2001 |
| WO | WO-03/006440 A2 | 1/2003 |
| WO | WO-2005/028473 | 3/2005 |

OTHER PUBLICATIONS

P. Ettmayer et al.: "Lessons Learned from Marketed and Investigational Prodrugs," Journal of Medicinal Chemistry, vol. 47, No. 10, May 6, 2004, pp. 2393-2404.
H. Bundgaard: "Design of Prodrugs: Bioreversible Derivatives for Various Functional Groups and Chemical Entities," Elsevier Science Publishers B. V., 1985, pp. 1-92.
S. Roerig et al.: "Discovery of the novel antithrombotic agent 5-chloro-n-((5S)-2-oxo-3[4-(3oxomorpholin-4-yl)phenyl]-,3-oxazolidin-5-yl)methyl)thiophene 2-carboxamide (Bay 59-7939): an oral, direct factor Xa inhibitor," Journal of Medicinal Chemistry, American Chemical Society, Washington, US, vol. 48, No. 22, Sep. 2005, pp. 5900-5908.
A. H. Kahns et al.: "N Acyl derivatives as prodrug forms for amides chemical stability and enzymatic hydrolysis of various N Acyl and N alkoxycarbonyl amide derivative," International Journal of Pharmaceutics (Kidlington), vol. 71, Nos. 1-2, 1991, pp. 31-44.
Ansell, et al.:"Managing Oral Anticoagulant Therapy," Chest, 2001, 119:22S-38S.
Casmiro-Garcia, et al.:"Progress in the Discovery of Factor Xa Inhibitors," Expert Opin. Ther. Patents, Feb. 2006, 16(2): 119-145.
Escolar, et al.:" Argatroban: A Direct Thrombin Inhibitor with Reliable and Predictable Anticoagulant Actions," Drugs of Today, 2006, 42(4):223-236.
Hauptman, et al.:"Synthetic Inhibitors of Thrombin and Factor Xa: From Bench to Bedside," Thrombosis Research, 1999, 93: 203-241.
Hirsh, et al.:"Oral Anticoagulants: Mechanism of Action, Clinical Effectiveness, and Optimal Therapeutic Range," Chest, 2001, 119:8S-21S.
Linkins, et al.:"New Anticoagulant Therapy," Annu. Rev. Med., 2005, 56:63-77.
Mackman:"Triggers, Targets and Treatments for Thrombosis," Nature, Feb. 2008, 451:914-918.
Quan, et al.:"The Race to an Orally Active Factor Xa Inhibitor: Recent Advances," Current Opinion in Drug Discovery & Development, 2004, 7(4): 460-469.
Raghavan, et al.:"Recent Advances in the Status and Targets of Antithrombotic Agents," Drugs of the Future, 2002, 27(7):669-683.
Reuf, et al.:"New Antithrombotic Drugs on the Horizon," Expert Opin. Investig. Drugs, 2003, 12(5): 781-797.
U.S. Appl. No. 13/328,532, filed Dec. 16, 2011.
U.S. Appl. No. 12/665,718, filed Dec. 20, 2009.
U.S. Appl. No. 12/665,729, filed Dec. 21, 2009.

* cited by examiner

*Primary Examiner* — Rebecca Anderson
(74) *Attorney, Agent, or Firm* — Karen B. King; Thomas C. Blankinship

(57) ABSTRACT

The present application relates to prodrug derivatives of 5-chloro-N-({(5S)-2-oxo-3-[4-(3-oxomorpholin-4-yl)phenyl]-1,3-oxazolidin-5-yl}methyl)thiophene-2-carboxamide, processes for their preparation, their use for the treatment and/or prophylaxis of diseases, and their use for the manufacture of medicaments for the treatment and/or prophylaxis of diseases, especially of thromboembolic disorders.

5 Claims, No Drawings

AMINOACYL PRODRUG DERIVATIVES AND MEDICAMENTS FOR TREATMENT OF THROMBOEMBOLIC DISORDERS

RELATED APPLICATIONS/PATENTS AND INCORPORATION BY REFERENCE

This application is a National Stage Application filed under 35 U.S.C. §371 based on International Application No. PCT/EP2007/007408, filed Aug. 23, 2007, which claims priority to German Patent Application Number 102006039589.1, filed Aug. 24, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to prodrug derivatives of 5-chloro-N-({(5S)-2-oxo-3-[4-(3-oxomorpholin-4-yl)phenyl]-1,3-oxazolidin-5-yl}methyl)thiophene-2-carboxamide, processes for their preparation, their use for the treatment and/or prophylaxis of diseases, and their use for the manufacture of medicaments for the treatment and/or prophylaxis of diseases, especially of thromboembolic disorders.

Prodrugs are derivatives of an active ingredient which undergo in vivo an enzymatic and/or chemical biotransformation in one or more stages before the actual active ingredient is liberated. A prodrug residue is ordinarily used in order to improve the profile of properties of the underlying active ingredient [P. Ettmayer et al., *J. Med. Chem.* 47, 2393 (2004)]. In order to achieve an optimal profile of effects it is necessary in this connection for the design of the prodrug residue as well as the desired mechanism of liberation to conform very accurately with the individual active ingredient, the indication, the site of action and the administration route. A large number of medicaments is administered as prodrugs which exhibit an improved bioavailability by comparison with the underlying active ingredient, for example achieved by improving the physicochemical profile, specifically the solubility, the active or passive absorption properties or the tissue-specific distribution. An example which may be mentioned from the wide-ranging literature on prodrugs is: H. Bundgaard (Ed.), *Design of Prodrugs: Bioreversible derivatives for various functional groups and chemical entities*, Elsevier Science Publishers B.V., 1985.

5-Chloro-N-({(5S)-2-oxo-3-[4-(3-oxomorpholin-4-yl)phenyl]-1,3-oxazolidin-5-yl}methyl)thiophene-2-carboxamide [BAY 59-7939, compound (A)] is an orally effective, direct inhibitor of the serine protease factor Xa which performs an essential function in regulating the coagulation of blood. The compound is currently undergoing in-depth clinical examination as a possible new active pharmaceutical ingredient for the prevention and therapy of thromboembolic disorders [S. Roehrig et al., *J. Med. Chem.* 48, 5900 (2005)].

(A)

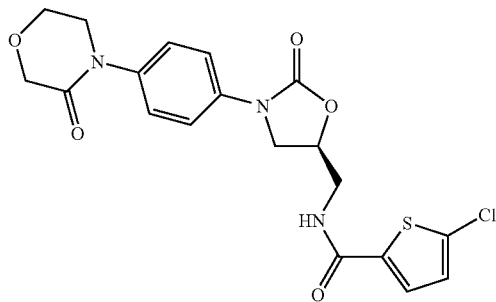

However, compound (A) has only a limited solubility in water and physiological media, making for example intravenous administration of the active ingredient difficult. It was therefore an object of the present invention to identify derivatives or prodrugs of compound (A) which have an improved solubility in the media mentioned and, at the same time, allow controlled liberation of the active ingredient (A) in the patient's body after administration.

WO 2005/028473 describes acyloxymethylcarbamate prodrugs of oxazolidinones which serve to increase the oral bioavailability. WO 01/00622 discloses acyl prodrugs of carbamate inhibitors of inosine-5'-monophosphate dehydrogenase. A further type of amide prodrugs for oxazolidinones which liberate the underlying active ingredient by a multi-stage activation mechanism is described in WO 03/006440.

The present invention relates to compounds of the general formula (I)

(I)

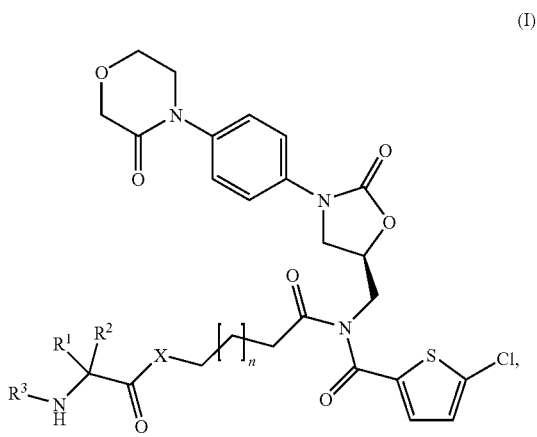

in which n is 1 or 2,

X is an oxygen atom, a sulphur atom or NH, $R^1$ is the side group of a natural α-amino acid or of its homologs or isomers, $R^2$ is hydrogen or methyl, $R^3$ is hydrogen, or $R^1$ and $R^3$ are linked via a $(CH_2)_3$ or $(CH_2)_4$ group and combine with the nitrogen or carbon atom to which they are attached to form a 5- or 6-membered ring, respectively, and also its salts, solvates and solvates of the salts.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

In the context of the present invention, the substituents have the following meaning unless otherwise specified:

The side group of an α-amino acid in the meaning of $R^1$ encompasses both the side groups of naturally occurring α-amino acids and the side groups of homologs and isomers of these α-amino acids. The α-amino acid may in this connection have both the L and the D configuration or else be a mixture of the L form and D form. Examples of side groups which may be mentioned are: hydrogen (glycine), methyl (alanine), propan-2-yl (valine), propan-1-yl (norvaline), 2-methylpropan-1-yl (leucine), 1-methylpropan-1-yl (isoleucine), butan-1-yl (norleucine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 3-guanidinopropan-1-yl (arginine), 3-ureido-propan-1-yl (citrulline). Preferred α-amino acid side groups in the meaning of $R^2$ are hydrogen (glycine), methyl (alanine), propan-2-yl (valine), propan-1-yl (norvaline), imidazol-4-ylmethyl (histidine), hydroxymethyl (serine), 1-hydroxyethyl (threonine), carbamoylmethyl (asparagine), 2-carbamoylethyl (glutamine), 4-aminobutan-1-yl (lysine), 3-aminopropan-1-yl (ornithine), 3-guanidinopropan-1-yl (arginine). The L configuration is preferred in each case.

If radicals in the compounds according to the invention are substituted, the radicals may, unless otherwise specified, be substituted one or more times. In the context of the present invention, all radicals which occur more than once have a mutually independent meaning. Substitution by one or two identical or different substituents is preferred. Substitution by one substituent is very particularly preferred.

Preference is given to compounds of the formula (I) in which n is 1 or 2,

X is an oxygen atom, a sulphur atom or NH, $R^1$ is hydrogen, methyl, propan-2-yl, propan-1-yl, 2-methylpropan-1-yl, imidazol-4-ylmethyl, hydroxymethyl, 1-hydroxyethyl, carboxymethyl, 2-carboxyethyl, carbamoylmethyl, 2-carbamoylethyl, 4-aminobutan-1-yl, 3-aminopropan-1-yl, 3-guanidinopropan-1-yl, benzyl or 4-hydroxybenzyl, $R^2$ is hydrogen or methyl, $R^3$ is hydrogen, or $R^1$ and $R^3$ are linked via a $(CH_2)_3$ or $(CH_2)_4$ group and combine with the nitrogen or carbon atom to which they are attached to form a 5- or 6-membered ring, respectively, and also its salts, solvates and solvates of the salts.

Preference is also given to compounds of the formula (I) in which n is 1 or 2,

X is NH, $R^1$ is hydrogen, methyl, propan-2-yl, 2-methylpropan-1-yl, imidazol-4-ylmethyl, hydroxymethyl, 1-hydroxyethyl, carboxymethyl, 2-carboxyethyl, carbamoylmethyl, 2-carbamoylethyl, 4-aminobutan-1-yl, benzyl or 4-hydroxybenzyl, $R^2$ is hydrogen, $R^3$ is hydrogen, and also its salts, solvates and solvates of the salts.

Preference is also given to compounds of the formula (I) in which n is 2.

Preference is also given to compounds of the formula (I) in which X is NH.

Preference is also given to compounds of formula (I) in which $R^1$ is hydrogen, methyl, propan-2-yl, 2-methylpropan-1-yl, imidazol-4-ylmethyl, hydroxymethyl, 1-hydroxyethyl, carboxymethyl, 2-carboxyethyl, carbamoylmethyl, 2-carbamoylethyl, 4-aminobutan-1-yl, 3-guanidinopropan-1-yl, benzyl or 4-hydroxybenzyl.

Preference is also given to compounds of formula (I) in which $R^1$ is hydrogen, methyl, propan-2-yl, 2-methylpropan-1-yl, imidazol-4-ylmethyl, hydroxymethyl, 1-hydroxyethyl, carboxymethyl, 2-carboxyethyl, carbamoylmethyl, 2-carbamoylethyl, 4-aminobutan-1-yl, benzyl or 4-hydroxybenzyl.

Preference is also given to compounds of formula (I) in which $R^2$ is hydrogen.

Preference is also given to compounds of formula (I) in which $R^3$ is hydrogen.

The present invention further provides a process for preparing the compounds of the formula (I), characterized in that either

[A] the compound of the formula

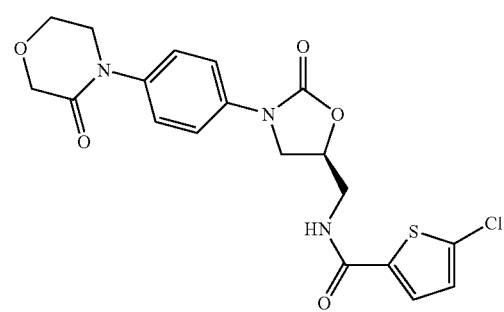

(A)

is initially converted in an inert solvent in the presence of a base with a compound of the formula

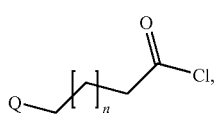

(II)

in which n has the meaning indicated above,
and
Q is a leaving group such as, for example, chlorine, bromine or iodine, into a compound of the formula

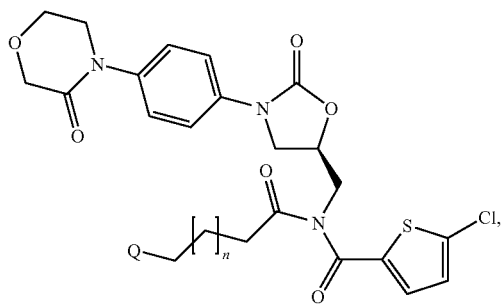

(III)

in which n and Q have the meaning indicated above
the latter is then reacted according to process
[A1] in an inert solvent with the caesium salt of an α-amino carboxylic acid or α-amino thiocarboxylic acid of the formula

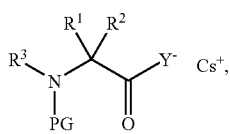

(IV)

in which $R^1$, $R^2$ and $R^3$ have the meaning indicated above,
PG is an amino protective group such as, for example, tert-butoxycarbonyl (Boc) or benzyloxycarbonyl (Z), and
Y is O or S,
to give a compound of the formula

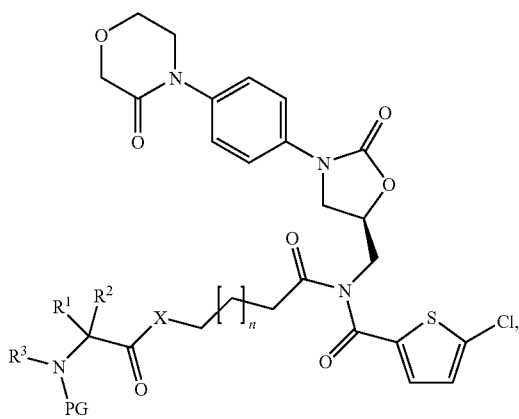

(V)

in which n, $R^1$, $R^2$, $R^3$ and PG have the meaning indicated above, and

X is O or S,
and subsequently the protective group PG is removed according to conventional methods to obtain a compound of the formula

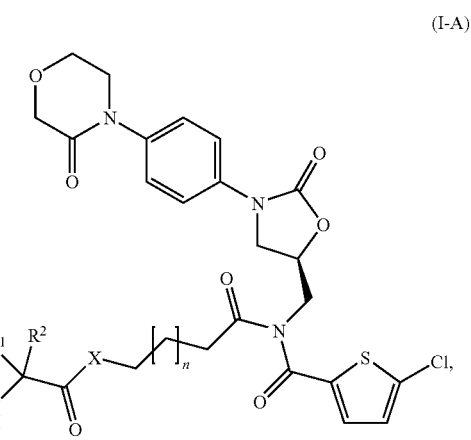

(I-A)

in which n, $R^1$, $R^2$ and $R^3$ have the meaning indicated above, and
X is O or S, or
[A2] in an inert solvent in the presence of a base with an α-amino thiocarboxylic acid of the formula

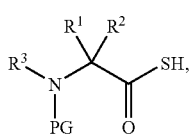

(VI)

in which $R^1$, $R^2$ and $R^3$ have the meaning indicated above,
PG is an amino protective group such as, for example, tert-butoxycarbonyl (Boc) or benzyloxycarbonyl (Z),
to give a compound of the formula

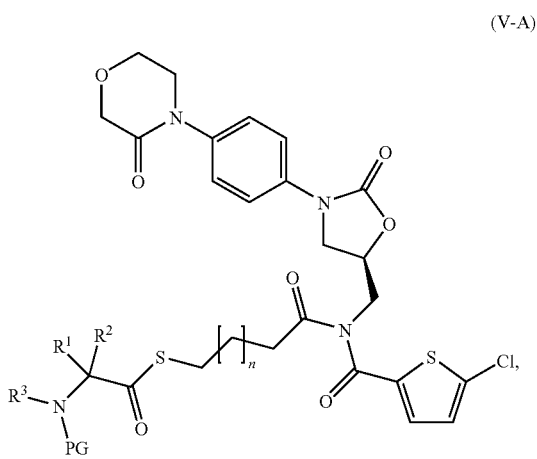

(V-A)

in which n, $R^1$, $R^2$, $R^3$ and PG have the meaning indicated above, and subsequently the protective group PG is removed according to conventional methods to obtain a compound of the formula (I-A)

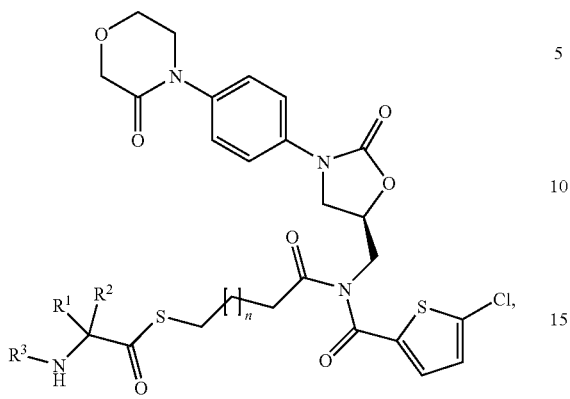

in which n, R$^1$, R$^2$ and R$^3$ have the meaning indicated above, or

[B] compound (A) is reacted in an inert solvent in the presence of a base with a compound of the formula (VII)

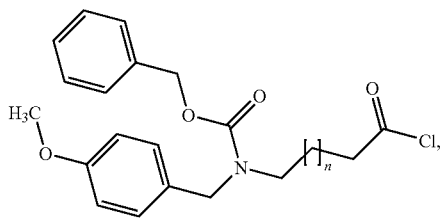

in which n has the meaning indicated above, to give a compound of the formula (VIII)

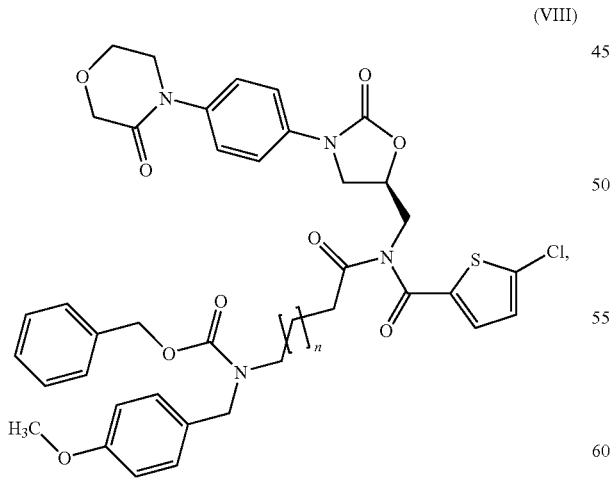

in which n has the meaning indicated above, subsequently the protective groups are removed according to conventional methods to obtain a compound of the formula (IX)

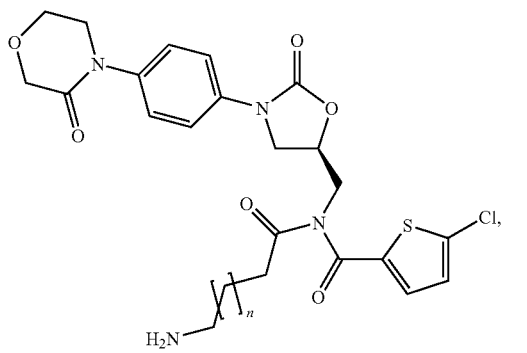

in which n has the meaning indicated above, and then in the presence of a base with a compound of the formula (X)

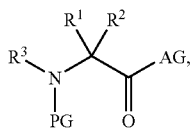

in which R$^1$, R$^2$ and R$^3$ have the meaning indicated above,

AG is hydroxyl or halogen, preferably chlorine or bromine, or combines with the carbonyl group to form an active ester, preferably an N-hydroxysuccinimide ester, or a mixed anhydride, preferably an alkyl carbonate, more preferably an ethyl carbonate, and PG is an amino protective group such as, for example, tert-butoxycarbonyl (Boc) or benzyloxycarbonyl (Z), to obtain a compound of the formula (XI)

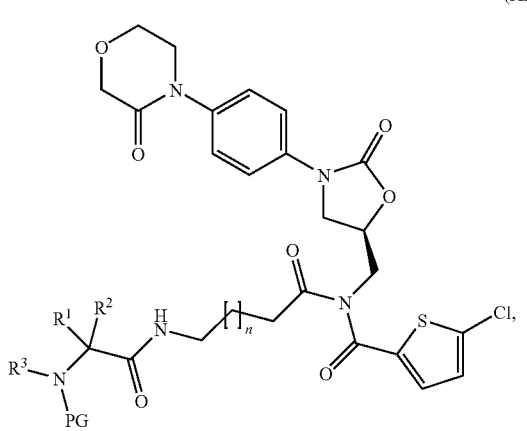

in which n, R$^1$, R$^2$, R$^3$ and PG have the meaning indicated above, and subsequently the protective group PG is removed according to conventional methods to obtain a compound of the formula

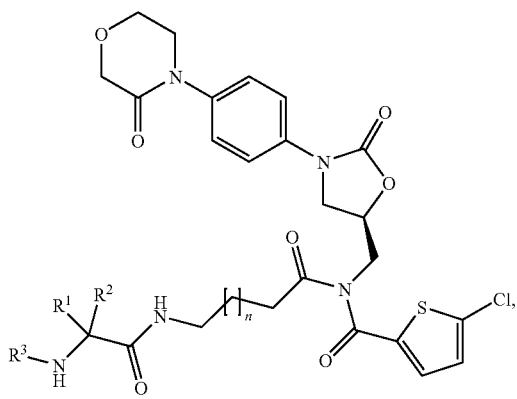

(I-B)

in which n, $R^1$, $R^2$ and $R^3$ have the meaning indicated above and the compounds of the formula (I-A) or (I-B) resulting in each case are converted where appropriate with the appropriate (i) solvents and/or (ii) acids into their solvates, salts and/or solvates of the salts.

The compounds of the formula (I-A), (I-B) and (IX) can also be present in the form of their salts. These salts can be converted where appropriate with the appropriate (i) solvents and/or (ii) bases into the free base.

Any functional groups present in the radical $R^1$ may, if advantageous or necessary, also be present in temporarily protected form in the reaction sequences described above. The introduction and removal of such protective groups, as well as of the protective group PG, takes place in this connection by conventional methods known from peptide chemistry [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984].

Such protective groups which are present where appropriate in $R^1$ may in this connection be removed at the same time as the elimination of PG or in a separate reaction step before or after the elimination of PG.

The amino protective group PG preferably used in the above processes is tert-butoxycarbonyl (Boc) or benzyloxycarbonyl (Z). Elimination of these protective groups and also the elimination of the protective groups in the process step (VIII)→(X) is carried out by conventional methods, preferably by reacting with a strong acid such as hydrogen chloride, hydrogen bromide or trifluoroacetic acid in an inert solvent such as dioxane, dichloromethane or acetic acid.

The inert solvents preferably used in process steps (A)+(II)→(III) and (A)+(VII)→(VIII) are tetrahydrofuran, N,N-dimethylformamide or dimethyl sulphoxide; N,N-dimethylformamide is particularly preferred. A particularly suitable base in these reactions is sodium hydride. The reactions mentioned are generally carried out in a temperature range from 0° C. to +40° C. under atmospheric pressure.

The inert solvents preferably used in process steps (III)+(VI)→(V-A) and (IX)+(X)→(XI) are tetrahydrofuran, N,N-dimethylformamide or dimethyl sulphoxide; N,N-dimethylformamide is particularly preferred. A particularly suitable base in these reactions is ethyl diisopropylamine. The reactions mentioned are generally carried out in a temperature range from 0° C. to +40° C. under atmospheric pressure.

Process step (III)+(IV)→(V) preferably takes place in N,N-dimethylformamide as solvent. The reaction is generally carried out in a temperature range from 0° C. to +50° C., preferably at +20° C. to +50° C., under atmospheric pressure. The reaction can also be carried out advantageously with ultrasound treatment.

The compounds of the formulae (II), (IV), (VI), (VII) and (X) are commercially available, known from the literature or can be prepared by processes customary in the literature. Preparation of compounds (A) is described in S. Roehrig et al., *J. Med. Chem.* 48, 5900 (2005).

Preparation of the compounds according to the invention can be illustrated by the following synthesis scheme:

Scheme

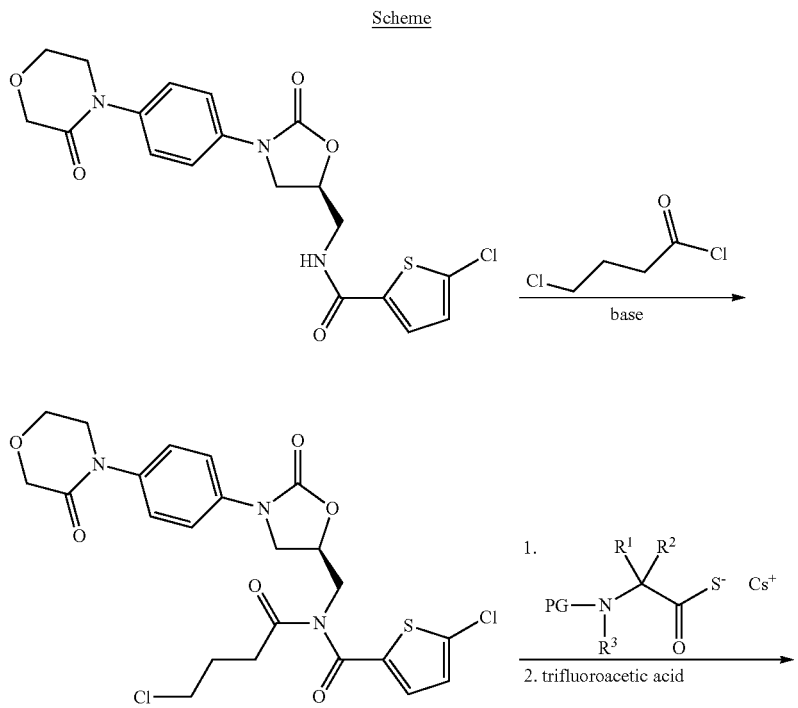

-continued

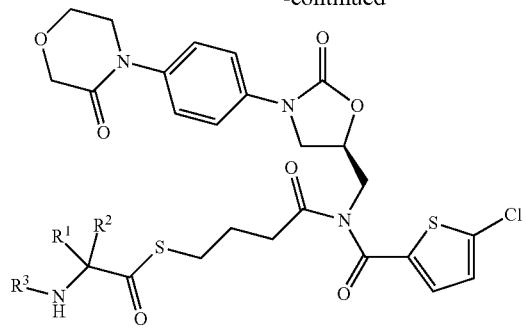

The compounds according to the invention and their salts represent useful prodrugs of the active ingredient compound (A). On the one hand, they show good stability for example at pH 4 and, on the other hand, they show efficient conversion into the active ingredient compound (A) in vivo. The compounds according to the invention moreover have good solubility in water and other physiologically tolerated media, making them suitable for therapeutic use especially on intravenous administration.

The present invention further relates to the use of the compounds according to the invention for the treatment and/or prophylaxis of disorders, preferably of thromboembolic disorders and/or thromboembolic complications.

The "thromboembolic disorders" include in the context of the present invention in particular disorders such as myocardial infarction with ST segment elevation (STEMI) and without ST segment elevation (non-STEMI), stable angina pectoris, unstable angina pectoris, reocclusions and restenoses following coronary interventions such as angioplasty or aortocoronary bypass, peripheral arterial occlusive diseases, pulmonary embolisms, deep venous thromboses and renal vein thromboses, transient ischaemic attacks, and thrombotic and thromboembolic stroke.

The substances are therefore also suitable for the prevention and treatment of cardiogenic thromboembolisms, such as, for example, cerebral ischaemias, stroke and systemic thromoboembolisms and ischaemias, in patients with acute, intermittent or persistent cardiac arrhythmias such as, for example, atrial fibrillation, and those undergoing cardioversion, also in patients with heart valve diseases or with artificial heart valves. The compounds according to the invention are additionally suitable for the treatment of disseminated intravascular coagulation (DIC).

Thromboembolic complications also occur in association with microangiopathic haemolytic anaemia, extracorporeal circulations, such as haemodialysis, and heart valve prostheses.

The compounds according to the invention are additionally suitable also for the prophylaxis and/or treatment of atherosclerotic vascular disorders and inflammatory disorders such as rheumatic disorders of the musculoskeletal system, furthermore likewise for the prophylaxis and/or treatment of Alzheimer's disease. The compounds according to the invention can additionally be employed for inhibiting tumour growth and metastasis formation, for microangiopathies, age-related macular degeneration, diabetic retinopathy, diabetic nephropathy and other microvascular disorders, and for the prevention and treatment of thromboembolic complications such as, for example, venous thromboembolisms in tumour patients, especially those undergoing major surgical procedures or chemotherapy or radiotherapy.

The present invention further relates to the use of the compounds according to the invention for the treatment and/or prophylaxis of disorders, especially of the aforementioned disorders.

The present invention further relates to the use of the compounds according to the invention for the manufacture of a medicament for the treatment and/or prophylaxis of disorders, especially of the aforementioned disorders.

The present invention further relates to a method for the treatment and/or prophylaxis of disorders, especially of the aforementioned disorders, using the compounds according to the invention.

The present invention further relates to medicaments comprising a compound according to the invention and one or more further active ingredients, especially for the treatment and/or prophylaxis of the aforementioned disorders. Examples of suitable combination active ingredients which may preferably be mentioned are:

lipid-lowering agents, especially HMG-CoA (3-hydroxy-3-methylglutarylcoenzyme A) reductase inhibitors;

coronary therapeutics/vasodilators, especially ACE (angiotensin converting enzyme) inhibitors, AII (angiotensin II) receptor antagonists; β-adrenoceptor antagonists; alpha-1 adrenoceptor antagonists; diuretics; calcium channel blockers; substances which bring about an increase in cyclic guanosine monophosphate (cGMP), such as, for example, stimulators of soluble guanylate cyclase;

plasminogen activators (thrombolytics/fibrinolytics) and compounds which increase thrombolysis/fibrinolysis, such as inhibitors of plasminogen activator inhibitor (PAI inhibitors) or inhibitors of the thrombin-activated fibrinolysis inhibitor (TAFI inhibitors);

substances having anticoagulant activity (anticoagulants);

platelet aggregation-inhibiting substances (platelet aggregation inhibitors, thrombocyte aggregation inhibitors);

fibrinogen receptor antagonists (glycoprotein Ib/IIIa antagonists);

and antiarrhythmics.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonary or nasal route. The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation, such as powder inhalers or nebulizers, or pharmaceutical forms which can be administered nasally, such as drops, solutions or sprays.

Parenteral administration is preferred, especially intravenous administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavours and/or odours.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations and Acronyms abs. absolute
Boc tert-butoxycarbonyl
DMF N,N-dimethylformamide
DMSO dimethyl sulphoxide
h hour(s)
HPLC high pressure, high performance liquid chromatography
LC-MS coupled liquid chromatography-mass spectrometry
min minute(s)
MS mass spectrometry
NMR nuclear magnetic resonance spectrometry
of theory (for yield)
Pd/C palladium on activated carbon
quant. quantitative (for yield)
$R_f$ retention index (for HPLC)
RT room temperature
UV ultraviolet spectrometry
v/v volume to volume ratio (of a solution)
Z benzyloxycarbonyl
LC-MS and HPLC Methods:
Method 1a (Preparative HPLC):
Column: VP 250/21 Nukleodur 100-5 C18 ec, Macherey & Nagel No. 762002; eluent A: water/0.01% trifluoroacetic acid, eluent B: acetonitrile/0.01% trifluoroacetic acid; gradient: 0 min 0% B→20 min 20% B→40 min 20% B→60 min 30% B→80 min 30% B→90 min 100% B→132 min 100% B; flow rate: 5 ml/min; temperature: RT; UV detection: 210 nm.

Method 1b (preparative HPLC): Column: Symmetry Prep™ C18 7 µM; 19×300 mm; Waters: eluent A: water/0.01% trifluoroacetic acid, eluent B: acetonitrile/0.01% trifluoroacetic acid; gradient: 0 min 0% B→20 min 20% B→40 min 20% B→60 min 30% B→80 min 30% B→90 min 100% B→132 min 100% B; flow rate: 5 ml/min; temperature: RT; UV detection: 210 nm.

Method 2 (analytical HPLC): Column: XTerra 3.9×150 WAT 186000478; eluent A: 10 ml of 70% perchloric acid in 2.5 liters of water, eluent B: acetonitrile; gradient: 0.0 min 20% B→1 min 20% B→4 min 90% B→9 min 90% B; temperature: RT; flow rate: 1 ml/min. In the variant of method 2a, the column is eluted at a temperature of 40° C.

Method 3 (LC-MS): Instrument: Micromass ZQ; HPLC instrument type; HP 1100 Series; UV DAD; column: Phenomenex Gemini 3µ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; temperature: 50° C.; UV detection: 210 nm.

Method 4 (LC-MS): Instrument: Micromass ZQ with HPLC HP 1100 Series; UV DAD; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; temperature: 50° C.; UV detection: 210 nm.

Method 5 (LC-MS): Instrument: Micromass Quattro LCZ with HPLC Agilent Series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; temperature: 50° C.; UV detection: 208-400 nm.

Method 6 (LC-MS): MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; temperature: 50° C.; UV detection: 210 nm.

Method 7 (chiral HPLC, analytical): Chiral silica gel phase (250 mm×4.6 mm) based on poly(N-methacryloyl-L-leucine dicyclopropylmethylamide); eluent: isohexane/ethyl acetate 35:65 (v/v); temperature: 24° C.; flow rate: 2 ml/min; UV detection: 270 nm.

Method 8 (chiral HPLC, analytical): Chiral silica gel phase (250 mm×4.6 mm) based on poly(N-methacryloyl-L-leucine tert-butylamide); eluent: isohexane/ethyl acetate 35:65 (v/v); temperature: 24° C.; flow rate: 2 ml/min; UV detection: 270 nm.

Method 9 (chiral HPLC, analytical): Chiral silica gel phase (250 mm×4.6 mm) based on poly(N-methacryloyl-L-leucine tert-butylamide); eluent: isohexane/ethyl acetate 65:35 (v/v); temperature: 24° C.; flow rate: 2 ml/min; UV detection: 270 nm.

Method 10 (chiral HPLC, preparative): Chiral silica gel phase (670 mm×40 mm) based on poly(N-methacryloyl-L-leucine dicyclopropylmethylamide); eluent: isohexane/ethyl acetate 25:75 (v/v); temperature: 24° C.; flow rate: 80 ml/min; UV detection: 270 nm.

Method 11 (chiral HPLC, preparative): Chiral silica gel phase (670 mm×40 mm) based on poly(N-methacryloyl-L-leucine tert-butylamide); eluent: isohexane/ethyl acetate 65:35 (v/v); temperature: 24° C.; flow rate: 50 ml/min; UV detection: 260 nm.

Method 12 (LC-MS): Instrument: Micromass Quattro LCZ with HPLC Agilent Series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.

Method 13 (LC-MS): Instrument: Micromass Platform LCZ with HPLC Agilent Series 1100; column: Thermo Hypersil GOLD 3μ, 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 14 (LC-MS): MS instrument type: Micromass ZQ; HPLC instrument type: Waters Alliance 2795; column: Merck Chromolith SpeedROD RP-18e 100 mm×4.6 mm; eluent A: 1 l of water+0.5 ml of 50% formic acid; eluent B: 1 l of acetonitrile+0.5 ml of 50% formic acid; gradient: 0.0 min 10% B→7.0 min 95% B→9.0 min 95% B; oven: 35° C.; flow rate: 0.0 min 1.0 ml/min→7.0 min 2.0 ml/min→9.0 min→2.0 ml/min; UV detection: 210 nm.

NMR Spectrometry:

NMR measurements are carried out at a proton frequency of 400.13 MHz or 500.13 MHz. The samples were normally dissolved in DMSO-$d_6$; temperature: 302 K.

Starting Compounds:

The starting material used is 5-chloro-N-({(5S)-2-oxo-3-[4-(3-oxomorpholin-4-yl)phenyl]-1,3-oxazolidin-5-yl}methyl)thiophene-2-carboxamide [compound (A)], preparation of which is described elsewhere [S. Roehrig et al., J. Med. Chem. 48, 5900 (2005)].

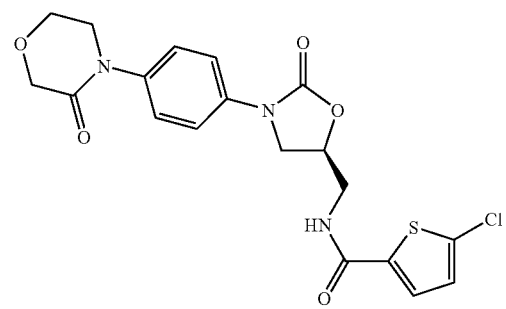

(A)

Example 1A

5-Chloro-N-(4-chlorobutanoyl)-N-({(5S)-2-oxo-3-[4-(3-oxomorpholin-4-yl)phenyl]-1,3-oxazolidin-5-yl}methyl)thiophene-2-carboxamide

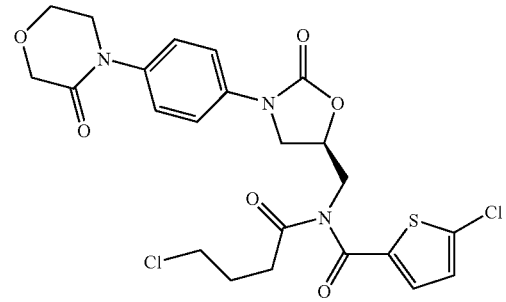 [SMILES: O=C(CCCCl)N(C[C@H]1CN(c2ccc(N3CCOCC3=O)cc2)C(=O)O1)C(=O)c1ccc(Cl)s1]

1 g (2.3 mmol) of 5-chloro-N-({(5S)-2-oxo-3-[4-(3-oxomorpholin-4-yl)phenyl]-1,3-oxazolidin-5-yl}methyl) thiophene-2-carboxamide [compound (A)] is dissolved in 100 ml of abs. DMF under argon. 110 mg (4.6 mmol) of sodium hydride (98% strength) are added, and the mixture is stirred at RT for 20 min. Then 4.37 g (30.97 mmol) of chlorobutanoyl chloride are added, keeping the reaction temperature at RT. The reaction mixture is stirred at RT for 16 h and is then admixed with 25 ml of water added gradually with cooling. Subsequently, 300 ml of ethyl acetate are added and a further 50 ml of water. The phases are separated and the ethyl acetate phase is concentrated in vacuo. The residue is stirred up with ethyl acetate and filtered. The mother liquor is concentrated and the residue is purified by flash chromatography on silica gel with toluene/ethanol 5:1 as eluent. The appropriate fractions which contain the target compound and also those which contain a bis-acylated compound formed after enolization are combined and the solvent is removed. The residue is admixed with a saturated solution of hydrogen chloride in dichloromethane and stirred at RT overnight. This is followed by concentrating in vacuo and the residue is again purified by flash chromatography on silica gel with toluene/ethanol 6:1 as eluent. The appropriate fractions are concentrated and the residue is lyophilized from dioxane to obtain 94 mg (7.5% of theory) of the target compound.

HPLC (method 2): $R_t$=5.23 min;

LC-MS (method 6): $R_t$=2.13 min; m/z=540 (M+H)$^+$.

Example 2A

5-Chloro-N-(4-chloropentanoyl)-N-({(5S)-2-oxo-3-[4-(3-oxomorpholin-4-yl)phenyl]-1,3-oxazolidin-5-yl}methyl)thiophene-2-carboxamide

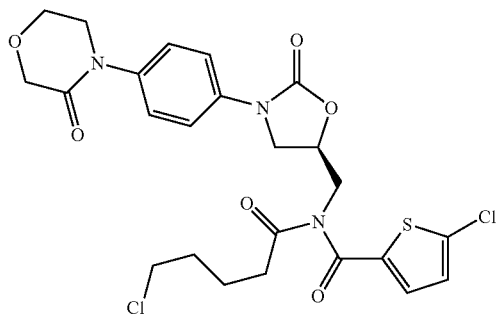 [SMILES: O=C(CCCCCl)N(C[C@H]1CN(c2ccc(N3CCOCC3=O)cc2)C(=O)O1)C(=O)c1ccc(Cl)s1]

Example 1A is repeated starting from 3 g (6.88 mmol) of compound (A) and 5-chloropentanoyl chloride to obtain 1008 mg (26% of theory) of the target compound.

HPLC (method 2): $R_t$=5.35 min;
LC-MS (method 6): $R_t$=2.22 min; m/z=554 (M+H)$^+$.

Example 3A

N-(4-Aminobutanoyl)-5-chloro-N-({(5S)-2-oxo-3-[4-(3-oxomorpholin-4-yl)phenyl]-1,3-oxazolidin-5-yl}methyl)thiophene-2-carboxamide hydrochloride

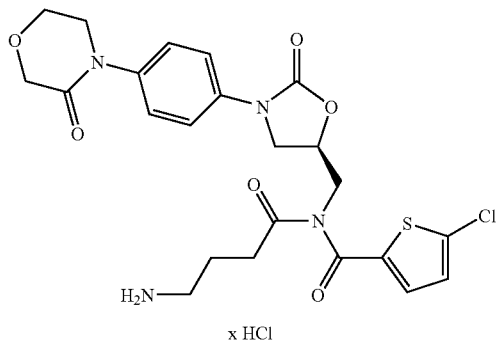 [SMILES: NCCCC(=O)N(C[C@H]1CN(c2ccc(N3CCOCC3=O)cc2)C(=O)O1)C(=O)c1ccc(Cl)s1]

x HCl

Stage a):

1.33 g (3.06 mmol) of compound (A) are dissolved in 75 ml of abs. DMF and admixed with 220 mg (9.2 mmol) of sodium hydride (98% strength), and the mixture is stirred at RT for 30 min. Then 11.5 g (30.6 mmol) of Example 5A, dissolved in 10 ml of abs. DMF, are added. The batch is stirred at RT for a further 15 min and then admixed with 20 ml of water. Thereafter, the batch is concentrated and the residue is taken up in 300 ml ethyl acetate and extracted three times with 300 ml of 10% sodium carbonate solution. The organic phase is separated off, concentrated and taken up in 50 ml of dichloromethane. Then 25 ml of diethyl ether are added. After brief stirring, undissolved residues are filtered off and the dichloromethane phase is concentrated. The residue is purified by flash chromatography on silica gel with ethyl acetate/toluene 5:1 as eluent. The appropriate fractions, which contain a bis-acylated by-product of mass M=1113, which is formed after enolization of the mono-acyl compound, are concentrated. Subsequently, the residue is stirred up with 10 ml of a saturated solution of hydrogen chloride in dichloromethane for 2 h, the enol ester initially formed being cleaved. This is followed by concentrating, and the remaining residue is purified by flash chromatography on silica gel with ethyl acetate/toluene 5:1 as eluent. The appropriate fractions are concentrated to obtain 151 mg (7% of theory) of the compound fully protected at the amino group.

HPLC (method 2): $R_t$=5.83 min
LC-MS (method 6): $R_t$=2.61 min; m/z=775 (M+H)$^+$.

Stage b):

151 mg (0.2 mmol) of this protected compound are stirred with 8 ml of anhydrous trifluoroacetic acid at RT overnight. The batch is concentrated under high vacuum, keeping the temperature at about 20° C. The residue is taken up in 100 ml of hydrochloric acid adjusted to pH 3 and extracted with 75 ml of dichloromethane and then twice with ethyl acetate. The aqueous phase is concentrated, and the residue is lyophilized from pH 3 hydrochloric acid to obtain 70 mg (64% of theory) of the target compound.

HPLC (method 2): $R_t$=4.13 min;
LC-MS (method 5): $R_t$=1.38 min; m/z=521 (M+H)$^+$.

Example 4A

N-(5-Aminopentanoyl)-5-chloro-N-({(5S)-2-oxo-3-[4-(3-oxomorpholin-4-yl)phenyl]-1,3-oxazolidin-5-yl}methyl)thiophene-2-carboxamide hydrochloride

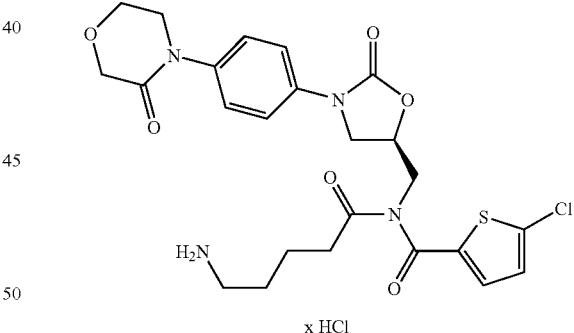

x HCl

Stage a):

2.83 g (6.5 mmol) of compound (A) are dissolved in 100 ml of abs. DMF under argon. 468 mg (19.5 mmol) of sodium hydride are added, and the mixture is stirred at RT for 30 min. Then 7.6 g (19.5 mmol) of Example 10A, dissolved in 10 ml of DMF, are added. Stirring is continued at RT for a further 15 min and the batch is then admixed with 20 ml of water added gradually. Thereafter the batch is concentrated and the residue is stirred up with 150 ml of saturated solution of hydrogen chloride in dichloromethane for 1 h, during which the bis-acyl compound initially formed after enolization, with mass M=1141, is cleaved. This is followed by concentrating and the residue is taken up in 700 ml of ethyl acetate and extracted twice with 200 ml each time of 10% sodium carbonate solution. The organic phase is separated off, concentrated and taken up in 30 ml of ethyl acetate and then admixed with 30 ml of diethyl ether. After brief stirring, undissolved residues are filtered off and the organic phase is concentrated. The residue is purified by flash chromatography on silica gel with ethyl acetate/toluene 4:1 as eluent. The appropriate fractions are concentrated and the residue is taken up in 10 ml of ethyl acetate. 100 ml of cold diethyl ether are added and the batch is left to stand at 0° C. for 30 min. After filtration, the residue is treated once more with 100 ml of diethyl ether. After renewed filtration, the filter residue is collected and dried to obtain 1 g (20% of theory) of the compound fully protected at the amino group.

HPLC (method 2): $R_t$=5.92 min
LC-MS (method 6): $R_t$=2.68 min; m/z=789 (M+H)$^+$.

Stage b):

1 g (1.3 mmol) of this protected compound are ultrasonicated in 70 ml of anhydrous trifluoroacetic acid for 6 h. The batch is concentrated under high vacuum, keeping the temperature at about 20° C. The residue is taken up in 350 ml of hydrochloric acid adjusted to pH 3 and, after 15 minutes of stirring at RT, extracted with 100 ml of dichloromethane. This is followed by extraction with 100 ml of ethyl acetate. The aqueous phase is separated off, then briefly distilled under high vacuum to remove remaining ethyl acetate, and finally lyophilized to obtain 586 mg (81% of theory) of the target compound.

HPLC (method 2): $R_t$=4.2 min;
LC-MS (method 6): $R_t$=1.17 min; m/z=535 (M+H)$^+$.

Example 5A

Benzyl (4-chloro-4-oxobutyl)(4-methoxybenzyl)carbamate

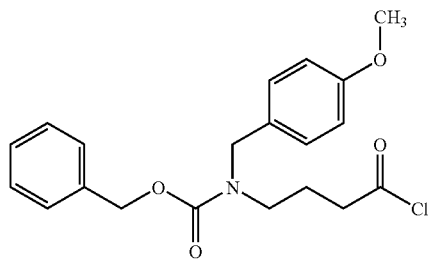 [SMILES: COc1ccc(CN(CCCC(=O)Cl)C(=O)OCc2ccccc2)cc1]

Example 10A is repeated starting from 4-aminobutyric acid.

Example 6A (2S)-2-[(tert-Butoxycarbonyl)amino]-3-methylbutanethio-S-acid

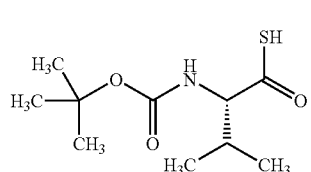

The title compound is prepared from Boc-valine similarly to a literature method [R. Michelot et al., *Bioorg. Med. Chem.* 1996, 4, 2201).

Example 7A

[(tert-Butoxycarbonyl)amino]ethanethio-S-acid

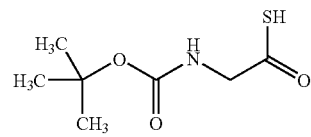

The title compound is prepared from Boc-glycine similarly to a literature method [R. Michelot et al., *Bioorg. Med. Chem.* 1996, 4, 2201).

Example 8A (2S)-2,6-Bis[(tert-butoxycarbonyl)amino]hexanethio-S-acid

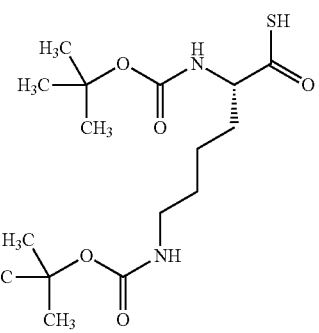

The title compound is prepared from bis-Boc-lysine similarly to a literature method [R. Michelot et al., *Bioorg. Med. Chem.* 1996, 4, 2201).

Example 9A (2S)-2-[(tert-Butoxycarbonyl)amino]propanethio-S-acid

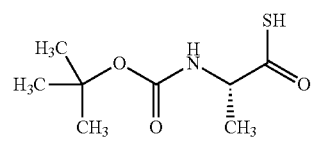

The title compound is prepared from Boc-alanine similarly to a literature method [R. Michelot et al., *Bioorg. Med. Chem.* 1996, 4, 2201).

Example 10A

Benzyl (5-chloro-5-oxopentyl)(4-methoxybenzyl)carbamate

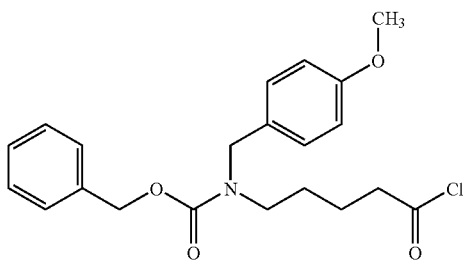 [SMILES: COc1ccc(CN(CCCCC(=O)Cl)C(=O)OCc2ccccc2)cc1]

10 g (85.4 mmol) of 5-aminovaleric acid, 17.4 g (128 mmol) of p-anisaldehyde and 10.3 g (85.4 mmol) of magnesium sulphate are taken up in 330 ml of ethanol and heated under reflux for 1 h. The solid is then filtered off and washed with ethanol, and subsequently a total of 1.94 g (51.2 mmol) of sodium borohydride are added in portions to the solution over the course of 15 min. Firstly 10 ml of water are added, and then 128 ml of a 2 M sodium hydroxide solution. After 5 min, the mixture is diluted with 300 ml of water and then extracted three times with 200 ml of ethyl acetate each time. The aqueous phase is adjusted to pH 2 with 4 M hydrochloric acid and concentrated in vacuo. The residue is purified by flash chromatography on silica gel with acetonitrile/water/acetic acid 5:1:0.1 as eluent. The appropriate fractions are concentrated and stirred with ethyl acetate and diethyl ether. The residue is then filtered off with suction and dried under high vacuum. 9.1 g (45% of theory) of the p-methoxybenzyl-protected amino acid are obtained.

The latter is taken up in 1.6 l of dioxane/water (1:1) and adjusted to pH 10 with sodium hydroxide solution, and then 12.97 g (76 mmol) of benzyl chlorocarbonate are added dropwise. After stirring at RT for 15 min, the dioxane is removed in vacuo and the remaining solution is adjusted to pH 2 with 2 M hydrochloric acid. The organic phase after extraction with ethyl acetate is washed twice with water. The organic phase is then concentrated and the residue is dried under high vacuum. This is followed by purification by flash chromatography on silica gel with acetonitrile as eluent. The appropriate fractions are concentrated and the residue is dried under high vacuum. 5.6 g (38% of theory) of the protected amino acid are obtained.

LC-MS (method 3): $R_t$=2.47 min; m/z=372 (M+H)$^+$.

5.6 g (15 mmol) of the 5-{[(benzyloxy)carbonyl](4-methoxybenzyl)amino}valeric acid are dissolved in 60 ml of dichloromethane, and 2.2 ml of thionyl chloride are added. The mixture is heated under reflux for 30 min. It is then concentrated in vacuo, and the residue is again mixed with dichloromethane and concentrated once again. A viscous oil remains and is dried under high vacuum. 5.7 g (98% of theory) of the target compound are obtained and are reacted further without further purification and characterization.

EXEMPLARY EMBODIMENTS

General Procedure 1 for Preparing Caesium Salts of Carboxylic Acids or Suitably Protected Amino Acid Derivatives 1 mmol of the appropriate carboxylic acid is dissolved in a mixture of 10 ml of dioxane and 10 ml of water, and 0.5 mmol of caesium carbonate is added. This is followed by lyophilization.

General Procedure 2 for Preparing Urethane-Protected N-Carboxyanhydrides of Suitably Protected Amino Acid Derivatives

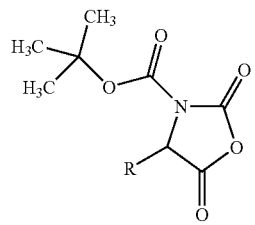

Urethane-protected N-carboxyanhydrides of amino acid derivatives are either commercially available or obtainable by following literature methods: M. Johnston et al. J. Org. Chem. 1985, 50, 2200; W. D. Fuller et al. J. Am. Chem. Soc. 1990, 112, 7414; S. Mobasheri et al. J. Org. Chem. 1992, 57, 2755.

General Procedure 3 for Preparing N-Hydroxysuccinimide Esters of Suitably Protected Amino Acid Derivatives

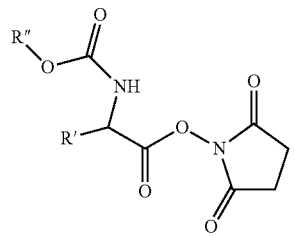

N-Hydroxysuccinimide esters of amino acid derivatives are either commercially available or obtainable by following standard methods of peptide chemistry.

Example 1

2-[[(5-Chloro-2-thienyl)carbonyl]({(5S)-2-oxo-3-[4-(3-oxomorpholin-4-yl)phenyl]-1,3-oxazolidin-5-yl}methyl)amino]-4-oxobutylglycinate hydrochloride

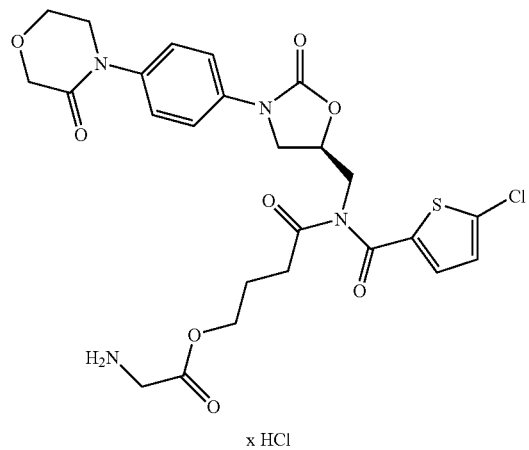 [SMILES: NCC(=O)OCCCC(=O)N(C[C@H]1CN(c2ccc(N3CCOCC3=O)cc2)C(=O)O1)C(=O)c1ccc(Cl)s1]

x HCl

Stage a):

14 mg (26 µmol) of Example 1A are dissolved with 9.5 mg (31 µmol) of the caesium salt of Boc-glycine (prepared from Boc-glycine by General Procedure 1) in 5 ml of DMF. Stirring at 50° C. for 16 h is followed by concentrating and the residue is purified by preparative HPLC (method 1a). The appropriate fractions are concentrated and dried under high vacuum to obtain 8 mg (45% of theory) of the protected title compound.

HPLC (method 2): $R_t$=5.18 min;

LC-MS (method 3): $R_t$=2.38 min; m/z=679 (M+H)$^+$.

Stage b):

7 mg (11 µmol) of the protected intermediate obtained in stage a) and still impure are admixed with 1 ml of a 22% strength solution of hydrogen chloride in dioxane. After 30 min, the mixture is concentrated in vacuo at 25° C. or below. The residue is purified by preparative HPLC (method 1a). The appropriate fractions are concentrated and subsequently lyophilized from dioxane to obtain 0.6 mg (8% of theory) of the title compound.

HPLC (method 2): $R_t$=4.2 min;

LC-MS (method 3): $R_t$=1.33 min; m/z=579 (M+H)$^+$.

Example 2

2-[[(5-Chloro-2-thienyl)carbonyl]({(5S)-2-oxo-3-[4-(3-oxomorpholin-4-yl)phenyl]-1,3-oxazolidin-5-yl}methyl)amino]-5-oxopentylglycinate hydrochloride

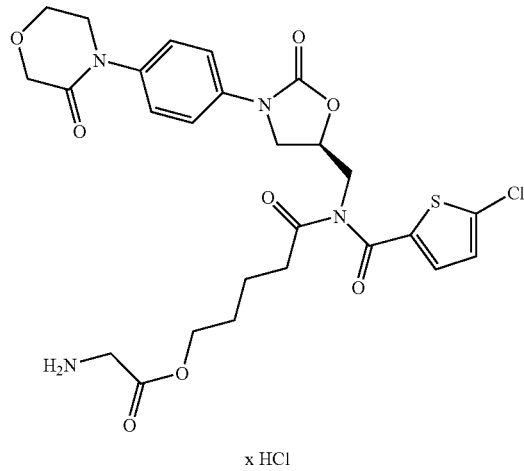 [SMILES: NCC(=O)OCCCCC(=O)N(C[C@H]1CN(c2ccc(N3CCOCC3=O)cc2)C(=O)O1)C(=O)c1ccc(Cl)s1]

x HCl

Stage a):

59 mg (106 µmol) of Example 2A are dissolved with 43 mg (138.4 µmol) of the caesium salt of Boc-glycine (prepared from Boc-glycine by General Procedure 1) in 10 ml of DMF. Stirring at 50° C. for 16 h is followed by concentrating and the residue is purified by preparative HPLC (method 1a). The appropriate fractions are concentrated and dried under high vacuum to obtain 26 mg (35% of theory) of the protected title compound.

HPLC (method 2): $R_t$=5.27 min;

LC-MS (method 6): $R_t$=2.23 min; m/z=693 (M+H)$^+$.

Stage b):

12 mg (17 µmol) of the protected intermediate obtained in stage a) are admixed with 3 ml of a 22% strength solution of hydrogen chloride in dioxane. After 30 min, the mixture is concentrated in vacuo at 25° C. or below. The residue is purified by preparative HPLC (method 1a). The appropriate fractions are concentrated and subsequently lyophilized from hydrochloric acid pH 4 to obtain 7.2 mg (66% of theory) of the title compound.

HPLC (method 2): $R_t$=4.32 min;

LC-MS (method 5): $R_t$=1.48 min; m/z=593 (M+H)$^+$.

Example 3

2-[[(5-Chloro-2-thienyl)carbonyl]({(5S)-2-oxo-3-[4-(3-oxomorpholin-4-yl)phenyl]-1,3-oxazolidin-5-yl}methyl)amino]-5-oxopentyl-L-valinate hydrochloride

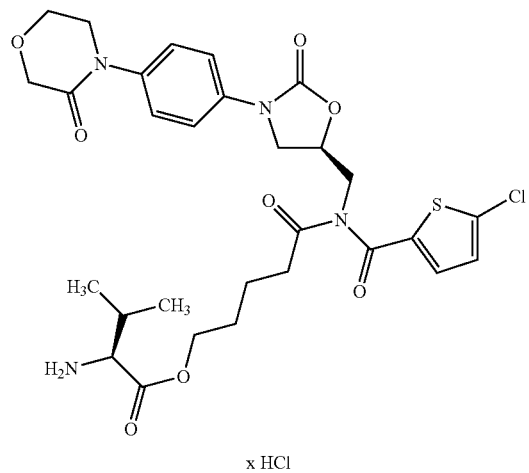 [SMILES: CC(C)[C@H](N)C(=O)OCCCCC(=O)N(C[C@H]1CN(c2ccc(N3CCOCC3=O)cc2)C(=O)O1)C(=O)c1ccc(Cl)s1]

x HCl

Stage a):

50 mg (90 µmol) of Example 2A are dissolved with 41 mg (117 µmol) of the caesium salt of Boc-valine (prepared from Boc-valine by General Procedure 1) in 10 ml of DMF. Stirring at 50° C. for 42 h is followed by concentrating and the residue is purified by preparative HPLC (method 1a). The appropriate fractions are concentrated and dried under high vacuum to obtain 26 mg (39% of theory) of the protected title compound.

HPLC (method 2): $R_t$=5.71 min;

LC-MS (method 6): $R_t$=2.56 min; m/z=733 (M−H)$^+$.

Stage b):

26 mg (35 µmol) of the protected intermediate obtained in stage a) are taken up in 5 ml of dichloromethane and are admixed with 2 ml of anhydrous trifluoroacetic acid. After 30 min, the mixture is concentrated in vacuo at 25° C. or below. The residue is stirred up with acetonitrile and the solvent is subsequently removed. The residue is lyophilized from hydrochloric acid pH 3 to obtain 24 mg (quant.) of the title compound.

HPLC (method 2): $R_t$=4.5 min;

LC-MS (method 3): $R_t$=1.52 min; m/z=635 (M+H)$^+$.

$^1$H NMR (500 MHz, DMSO-d$_6$): δ=0.95 (2d, 6H), 1.65 (m, 4H), 2.15 (m, 1H), 2.6 (m, 2H), 3.7 (t, 2H), 3.8 (dd, 1H), 3.9 (d, 1H), 3.95 (t, 2H), 4.1-4.3 (m, 7H), 4.9 (m, 1H), 7.3 (d, 1H), 7.4 (d, 2H), 7.5 (d, 2H), 7.6 (d, 1H), 8.3 (m, 3H).

Example 4

S-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)(2S)-2-amino-3-methylbutanethioate hydrochloride

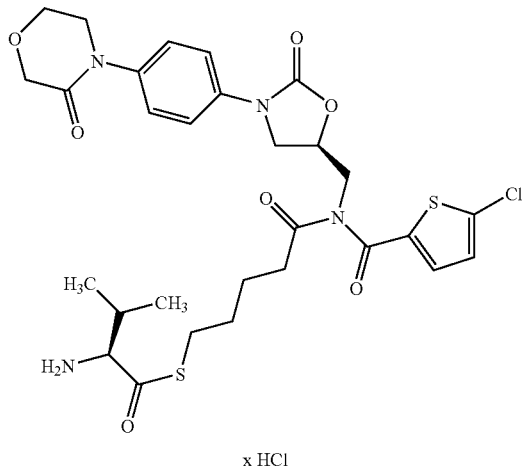

x HCl

Stage a):
50 mg (90 µmol) of Example 2A are dissolved with 42 mg (180 µmol) of Example 6A in 10 ml of DMF. 16 µl of ethyldiisopropylamine are added and the mixture is stirred at 60° C. for 16 h. This is followed by concentrating and the residue is purified by preparative HPLC (method 1b). The appropriate fractions are concentrated and dried under high vacuum to obtain 17 mg (25% of theory) of the protected title compound.

HPLC (method 2): $R_t$=5.56 min;

Stage b):
17 mg (23 µmol) of the protected intermediate obtained in stage a) are admixed with 3 ml of anhydrous trifluoroacetic acid. After 15 min, the mixture is concentrated in vacuo at 25° C. or below. The residue is taken up in hydrochloric acid adjusted to pH 3 and extracted twice with a little dichloromethane and ethyl acetate. The aqueous phase is concentrated and subsequently lyophilized from hydrochloric acid pH 3 to obtain 7 mg (45% of theory) of the title compound.

HPLC (method 2): $R_t$=4.65 min;
LC-MS (method 6): $R_t$=1.5 min; m/z=651 (M+H)$^+$.
$^1$H NMR (500 MHz, DMSO-d$_6$): δ=0.95 and 1.0 (2d, 6H), 1.5-1.7 (m, 4H), 2.15 (m, 1H), 2.55 (t, 2H), 3.0 (m, 2H), 3.7 (t, 2H), 3.8 (dd, 1H), 3.95 (t, 2H), 4.1-4.3 (m, 6H), 4.9 (m, 1H), 7.3 (d, 1H), 7.4 (d, 2H), 7.5 (d, 2H), 7.6 (d, 1H), 8.3 (m, 3H).

Example 5

S-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)aminoethanethioate hydrochloride

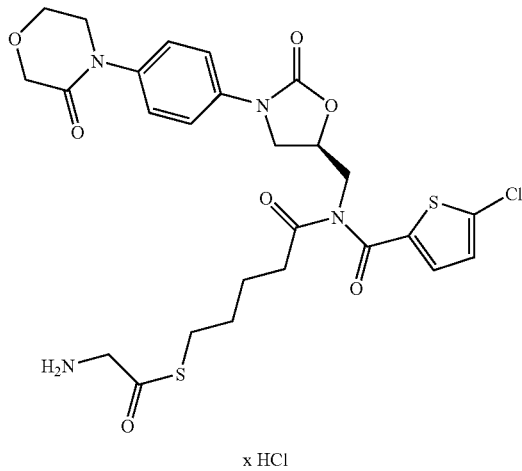

x HCl

Stage a):
50 mg (90 µmol) of Example 2A are dissolved with 52 mg (271 µmol) of Example 7A in 15 ml of DMF. 16 µl of ethyldiisopropylamine are added and the mixture is stirred at 60° C. for 40 h. During this period, a further 52 mg of Example 7A are added five times. This is followed by concentrating. The residue is taken up in ethyl acetate and extracted twice with 10% sodium carbonate solution. The organic phase is concentrated and the residue is then purified by preparative HPLC (method 1a). The appropriate fractions with the target compound still contain starting material. They are freed of solvent in vacuo and used in that form in the next stage. 38 mg (59% of theory; crude product) of the protected title compound are obtained.

HPLC (method 2): $R_t$=5.43 min;

Stage b):
37 mg (52 µmol) of the protected intermediate obtained in stage a) are admixed with 3 ml of anhydrous trifluoroacetic acid. After 15 min, the mixture is concentrated in vacuo at 25° C. or below. The residue is purified by preparative HPLC (method 1a). In the process, remaining starting material is removed. The appropriate fractions are concentrated and subsequently lyophilized from hydrochloric acid pH 3 to obtain 8 mg (24% of theory) of the title compound.

HPLC (method 2): $R_t$=4.4 min;
LC-MS (method 12): $R_t$=2.1 min; m/z=609 (M+H)±.
$^1$H NMR (500 MHz, DMSO-d$_6$): δ=1.5-1.7 (m, 4H), 2.55 (m, 2H), 3.0 (t, 2H), 3.7 (t, 2H), 3.8 (dd, 1H), 3.95 (t, 2H), 4.05-4.25 (m, 7H), 4.9 (m, 1H), 7.3 (d, 1H), 7.4 (d, 2H), 7.5 (d, 2H), 7.6 (d, 1H), 8.3 (m, 3H).

Example 6

S-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)(2S)-2,6-diaminohexanethioate dihydrochloride

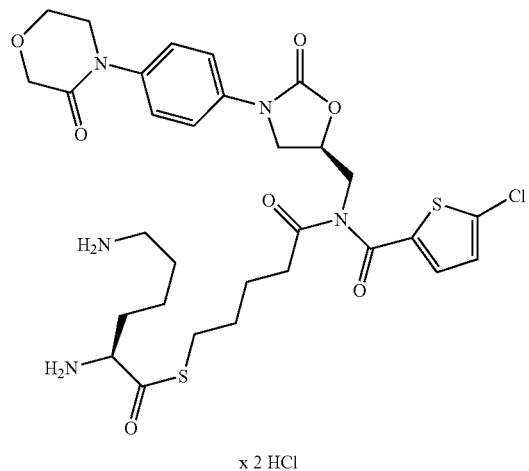 [SMILES: NCCCC[C@H](N)C(=O)SCCCCC(=O)N(C[C@H]1CN(c2ccc(N3CCOCC3=O)cc2)C(=O)O1)C(=O)c1ccc(Cl)s1]

x 2 HCl

Stage a):
50 mg (90 µmol) of Example 2A are dissolved with 98 mg (271 µmol) of Example 8A in 15 ml of DMF. 16 µl of ethyldiisopropylamine are added and the mixture is stirred at 60° C. for 40 h. During this period, a further 98 mg of Example 8A are added five times. This is followed by concentrating. The residue is taken up in ethyl acetate and extracted twice with 10% sodium carbonate solution. The organic phase is concentrated and the residue is then purified by preparative HPLC (method 1a). The appropriate fractions with the target compound are concentrated and purified a second time by means of preparative HPLC (method 1a). The fractions which contain the target compound in pure form are combined and concentrated to obtain 26 mg (33% of theory) of the protected title compound.

HPLC (method 2): $R_t$=5.85 min;

Stage b):

25 mg (28 µmol) of the protected intermediate obtained in stage a) are admixed with 5 ml of anhydrous trifluoroacetic acid. After 5 min the mixture is concentrated in vacuo at 25° C. or below. The residue is purified by preparative HPLC (method 1a). The appropriate fractions are concentrated and subsequently lyophilized from hydrochloric acid pH 3 to obtain 10 mg (49% of theory) of the title compound.

HPLC (method 2): $R_t$=4.2 min;

LC-MS (method 13): $R_t$=2.6 min; m/z=680 (M+H)$^+$.

$^1$H NMR (500 MHz, DMSO-d$_6$): δ=1.3-1.5 (m, 2H), 1.5-1.7 (m, 6H), 1.7-1.9 (m, 2H), 2.55 (m, 2H), 2.75 (m, 2H), 2.95 (t, 2H), 3.7 (t, 2H), 3.8 (dd, 1H), 3.95 (t, 2H), 4.1-4.3 (m, 6H), 4.9 (m, 1H), 7.3 (d, 1H), 7.4 (d, 2H), 7.5 (d, 2H), 7.6 (d, 1H), 7.85 (m, 3H), 8.5 (m, 3H).

Example 7

S-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)(2S)-2-aminopropanethioate hydrochloride

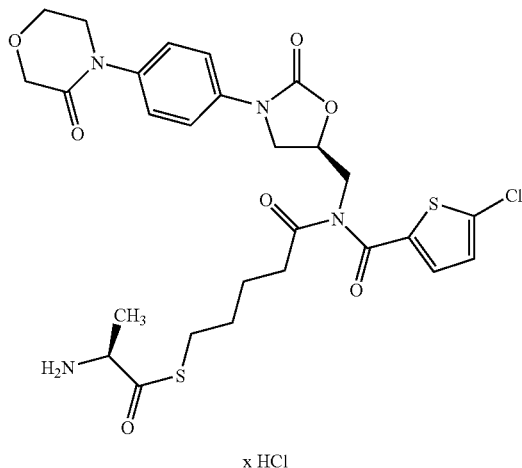 [SMILES: C[C@H](N)C(=O)SCCCCC(=O)N(C[C@H]1CN(c2ccc(N3CCOCC3=O)cc2)C(=O)O1)C(=O)c1ccc(Cl)s1]

x HCl

Stage a):

50 mg (90 µmol) of Example 2A are dissolved with 55 mg (270 µmol) of Example 9A in 15 ml DMF. 16 µl of ethyldiisopropylamine are added and the mixture is stirred at 60° C. for 40 h. During this period, a further 55 mg of Example 9A are added five times. This is followed by concentrating. The residue is taken up in ethyl acetate and extracted twice with 10% sodium carbonate solution. The organic phase is concentrated and the residue is then purified by preparative HPLC (method 1a). The appropriate fractions are combined and freed of solvent to obtain 28 mg (43% of theory) of the protected title compound.

Stage b):

28 g (19 µmol) of the protected intermediate obtained in stage a) are admixed with 3 ml of anhydrous trifluoroacetic acid. After 15 min the batch is concentrated in vacuo at 25° C. or below. The residue is purified by preparative HPLC (method 1a). The appropriate fractions are concentrated and subsequently lyophilized from hydrochloric acid pH 3 to obtain 10 mg (81% of theory) of the title compound.

HPLC (method 2): $R_t$=4.46 min;

LC-MS (method 14): $R_t$=3.37 min; m/z=623 (M+H)$^+$.

$^1$H NMR (500 MHz, DMSO-d$_6$): δ=1.45 (d, 3H), 1.5-1.7 (m, 4H), 2.55 (t, 2H), 2.95 (t, 2H), 3.7 (t, 2H), 3.8 (dd, 1H), 3.95 (t, 2H), 4.1-4.25 (m, 5H), 4.3 (q, 1H), 4.9 (m, 1H), 7.3 (d, 1H), 7.4 (d, 2H), 7.5 (d, 2H), 7.6 (d, 1H), 8.4 (m, 3H).

Example 8

S-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-4-oxobutyl)(2S)-2-amino-3-methylbutanethioate hydrochloride

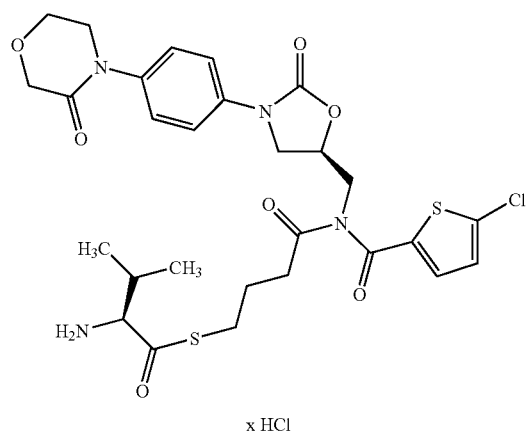 [SMILES: CC(C)[C@H](N)C(=O)SCCCC(=O)N(C[C@H]1CN(c2ccc(N3CCOCC3=O)cc2)C(=O)O1)C(=O)c1ccc(Cl)s1]

x HCl

Stage a):

48 mg (89 µmol) of Example 1A are dissolved with 62 mg (266 µmol) of Example 6A in 15 ml of DMF. 16 µl of ethyldiisopropylamine are added and the mixture is stirred at 60° C. for 40 h. During this period, a further 62 mg of Example 6A are added five times. This is followed by concentrating. The residue is taken up in ethyl acetate and extracted twice with 10% sodium carbonate solution. The organic phase is concentrated and the residue is then purified by preparative HPLC (method 1a). The appropriate fractions are concentrated and dried under high vacuum to obtain 22 mg (34% of theory) of the protected title compound.

HPLC (method 2): $R_t$=5.76 min;

Stage b):

22 mg (30 µmol) of the protected intermediate obtained in stage a) are admixed with 3 ml of anhydrous trifluoroacetic acid. After 5 min the mixture is concentrated in vacuo at 25° C. or below. The residue is purified by preparative HPLC (method 1a). The appropriate fractions are concentrated and subsequently lyophilized from hydrochloric acid pH 3 to obtain 11 mg (52% of theory) of the title compound.

HPLC (method 2): $R_t$=4.55 min;

LC-MS (method 6): $R_t$=1.43 min; m/z=637 (M+H)$^+$.

$^1$H-NMR (500 MHz, DMSO-d$_6$): δ=0.95 and 1.0 (2d, 6H), 1.8-1.9 (m, 2H), 2.2 (m, 1H), 2.65 (m, 2H), 3.0 (m, 2H), 3.7 (t, 2H), 3.8 (dd, 1H), 3.95 (t, 2H), 4.1-4.3 (m, 6H), 4.9 (m, 1H), 7.3 (d, 1H), 7.4 (d, 2H), 7.5 (d, 2H), 7.65 (d, 1H), 8.4 (m, 3H).

Example 9

5-Chloro-N-[4-(glycylamino)butanoyl]-N-({(5S)-2-oxo-3-[4-(3-oxomorpholin-4-yl)phenyl]-1,3-oxazolidin-5-yl}methyl)thiophene-2-carboxamide hydrochloride

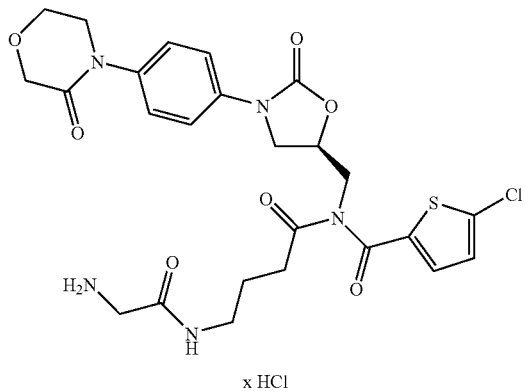 [SMILES: NCC(=O)NCCCC(=O)N(C[C@H]1CN(c2ccc(N3CCOCC3=O)cc2)C(=O)O1)C(=O)c1ccc(Cl)s1]

x HCl

Stage a):
40 mg (72 µmol) of Example 3A are dissolved with 17 mg (86 µmol) of tert-butyl 2,5-dioxo-1,3-oxazolidine-3-carboxylate in 5 ml of DMF. 13 µl of ethyldiisopropylamine are added a little at a time and stirring is continued at RT for a further 10 min. The batch is subsequently concentrated and the residue is then purified by preparative HPLC (method 1a). The appropriate fractions are concentrated and dried under high vacuum to obtain 22 mg (44% of theory) of the protected title compound.
HPLC (method 2): $R_t$=4.74 min;
LC-MS (method 5): $R_t$=2.07 min; m/z=678 (M+H)$^+$.

Stage b):
22 mg (32 µmol) of the protected intermediate obtained in stage a) are taken up in 10 ml of a saturated solution of hydrogen chloride in dioxane. 1 ml of water is added and the batch is stirred at RT for 5 min. After 5 min, the batch is concentrated in vacuo at 25° C. or below. The residue is purified by preparative HPLC (method 1b). The appropriate fractions are concentrated and subsequently lyophilized from hydrochloric acid pH 3 to obtain 4 mg (21% of theory) of the title compound.
HPLC (method 2): $R_t$=4.14 min;
LC-MS (method 3): $R_t$=1.26 min; m/z=578 (M+H)$^+$.

Example 10

5-Chloro-N-[4-(glycylamino)pentanoyl]-N-({(5S)-2-oxo-3-[4-(3-oxomorpholin-4-yl)phenyl]-1,3-oxazolidin-5-yl}methyl)thiophene-2-carboxamide hydrochloride

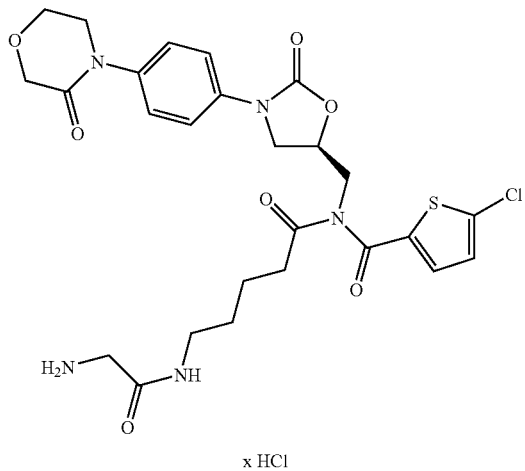 [SMILES: NCC(=O)NCCCCC(=O)N(C[C@H]1CN(c2ccc(N3CCOCC3=O)cc2)C(=O)O1)C(=O)c1ccc(Cl)s1]

x HCl

Stage a):
35 mg (61 µmol) of Example 3A are dissolved with 37 mg (184 µmol) of tert-butyl 2,5-dioxo-1,3-oxazolidine-3-carboxylate in 5 ml of DMF. 12 µl of ethyldiisopropylamine are added a little at a time and stirring is continued at RT for a further 10 min. The batch is subsequently concentrated and the residue is then purified by preparative HPLC (method 1a). The appropriate fractions are concentrated and dried under high vacuum to obtain 15 mg (36% of theory) of the protected title compound.
HPLC (method 2): $R_t$=4.85 min;
LC-MS (method 6): $R_t$=1.95 min; m/z=692 (M+H)$^+$.

Stage b):
15 mg (22 µmol) of the protected intermediate obtained in stage a) are taken up in 3 ml of a saturated solution of hydrogen chloride in dioxane and a drop of water is added. After stirring for 10 min at RT the batch is concentrated in vacuo at 25° C. or below. The residue is taken up in 30 ml of aqueous hydrochloric acid (pH 3) and extracted twice with dichloromethane and twice with ethyl acetate. The aqueous phase is concentrated and subsequently lyophilized from hydrochloric acid pH 3 to obtain 8 mg (58% of theory) of the title compound.
HPLC (method 2): $R_t$=4.24 min;
LC-MS (method 3): $R_t$=1.36 min; m/z=592 (M+H)$^+$.

Example 11

N-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)-L-prolineamide hydrochloride

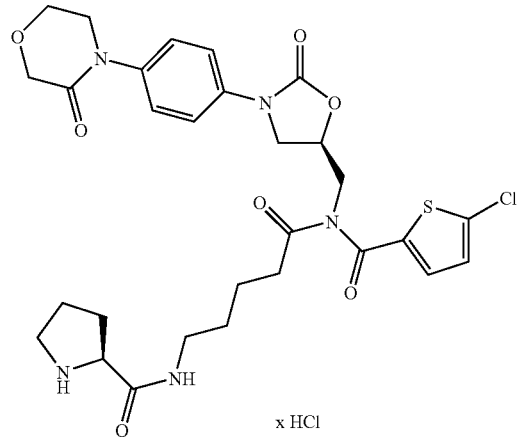 [SMILES: O=C(NCCCCC(=O)N(C[C@H]1CN(c2ccc(N3CCOCC3=O)cc2)C(=O)O1)C(=O)c1ccc(Cl)s1)[C@@H]1CCCN1 ; "x HCl"]

x HCl

Stage a):
50 mg (87 µmol) of Example 4A are initially charged with 47 mg (175 µmol) of benzyl (2S)-2-(chlorocarbonyl)pyrrolidine-1-carboxylate in 80 ml of dichloromethane. 3 portions of 263 µmol of a 0.1 M solution of ethyldiisopropylamine dissolved in DMF are added within 3 minutes and stirring is continued at RT for a further 10 min. This is followed by acidification with acetic acid and concentrating. The residue is taken up in 2 ml of DMF and then purified by preparative HPLC (method 1b). The appropriate fractions are concentrated and dried under high vacuum to obtain 40 mg (60% of theory) of the protected title compound.
HPLC (method 2): $R_t$=5.05 min;

Stage b):

40 mg (52 µmol) of the protected intermediate obtained in stage a) are taken up in 40 ml of anhydrous trifluoroacetic acid. Stirring at RT for 16 h is followed by concentrating in vacuo at 25° C. or below, and the residue is purified by preparative HPLC (method 1b). The appropriate fractions are concentrated and subsequently lyophilized from hydrochloric acid pH 3 to obtain 16 mg (46% of theory) of the title compound.

HPLC (method 2): $R_t$=4.28 min;

LC-MS (method 3): $R_t$=1.39 min; m/z=632 (M+H)$^+$.

$^1$H NMR (500 MHz, DMSO-d$_6$): δ=1.4 (m, 2H), 1.55 (m, 2H), 1.9 m (2H), 1.8 and 2.25 (2m, 2H), 2.55 (m, 2H), 3.0-3.3 (m, 4H), 3.7 (t, 2H), 3.8 (dd, 1H), 3.95 (t, 2H), 4.05-4.25 (m, 6H), 4.9 (m, 1H), 7.3 (d, 1H), 7.4 (d, 2H), 7.5 (d, 2H), 7.6 (d, 1H), 8.5 (m, 2H).

Example 12

N-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)-L-histidinamide hydrochloride

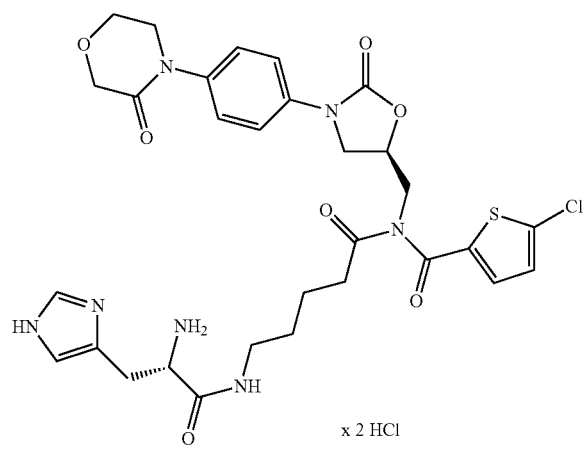 [SMILES: N[C@@H](Cc1c[nH]cn1)C(=O)NCCCCC(=O)N(C[C@H]1CN(c2ccc(N3CCOCC3=O)cc2)C(=O)O1)C(=O)c1ccc(Cl)s1 ; "x 2 HCl"]

Stage a):

199 mg (441 µmol) of 2,5-dioxopyrrolidin-1-yl N,1-bis(tert-butoxycarbonyl)-L-histidinate are initially charged together with 661 µl of a 0.1M solution of ethyldiisopropylamine in DMF in 1 ml of DMF. 42 mg (73 µmol) of Example 4A dissolved in 2.5 ml of DMF are added dropwise, via a syringe, over a period of 30 min. Stirring at RT for 30 min is followed by concentrating and the residue is purified by flash chromatography initially with acetonitrile and then with acetonitrile/water 10:1 as eluent. The appropriate fractions which contain still impure target compound are combined and concentrated in vacuo. The residue is then purified once more by preparative HPLC (method 1a). The appropriate fractions which contain a mixture of the bis-Boc-protected example and the mono-Boc-protected example are concentrated and dried under high vacuum to obtain 18 mg (28% of theory) of the protected title compound.

HPLC (method 2): $R_t$=4.48 min; 4.92 min

LC-MS (method 3): $R_t$=1.60 min; m/z=772 (M+H)$^+$; $R_t$=2.58 min; m/z=872 (M+H)$^+$.

Stage b):

18 mg of the mixture of the bis-Boc-protected intermediate and the mono-Boc-protected intermediate are taken up in 4 ml of anhydrous trifluoroacetic acid and stirred at RT for 20 min.

Then the batch is concentrated in vacuo at 25° C. or below and the residue is subsequently lyophilized twice from hydrochloric acid pH 3 to obtain 15 mg (98% of theory) of the title compound.

HPLC (method 2): $R_t$=4.12 min;

LC-MS (method 3): $R_t$=1.09 min; m/z=672 (M+H)$^+$.

$^1$H NMR (500 MHz, DMSO-d$_6$): δ=1.35 (m, 2H), 1.5 (m, 2H), 2.55 (m, 2H), 3.0-3.3 (m, 4H), 3.7 (t, 2H), 3.8 (dd, 1H), 3.95 (t, 2H), 4.1-4.3 (m, 6H), 4.95 (m, 1H), 7.3 (d, 1H), 7.4 (d, 2H), 7.45 (s, 1H), 7.5 (d, 2H), 7.65 (d, 1H), 8.5 (m, 3H), 8.7 (t, 1H), 9.0 (s, 1H).

Example 13

N-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)-L-valinamide hydrochloride

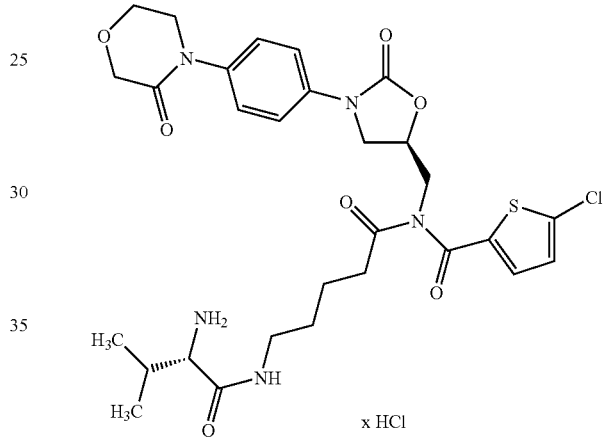

Stage a):

50 mg (87 µmol) of Example 4A are initially charged together with 64 mg (262 µmol) of tert-butyl (4S)-4-isopropyl-2,5-dioxo-1,3-oxazolidine-3-carboxylate in 20 ml of dichloromethane. 874 µl of a 0.1M solution of ethyldiisopropylamine in DMF are added a little at a time and stirring is continued at RT for a further 10 min. The batch is subsequently diluted with dichloromethane and extracted twice with water. The organic phase is concentrated and the residue is then purified by preparative HPLC (method 1b). The appropriate fractions are concentrated and dried under high vacuum to obtain 4.5 mg (7% of theory) of the protected title compound.

HPLC (method 2): $R_t$=5.14 min;

Stage b):

4.5 mg (6 µmol) of the protected compound are taken up in 2 ml of anhydrous trifluoroacetic acid and stirred at RT for 15 min. The batch is then concentrated in vacuo at 25° C. or below and the residue is taken up in 20 ml of dilute hydrochloric acid (pH 3) and extracted twice with dichloromethane and once with ethyl acetate. The aqueous phase is then lyophilized from hydrochloric acid pH 3 to obtain 3 mg (73% of theory) of the title compound.

HPLC (method 2): $R_t$=4.36 min;

LC-MS (method 3): $R_t$=1.46 min; m/z=634 (M+H)$^+$.

Example 14

N-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)-L-lysinamide hydrochloride

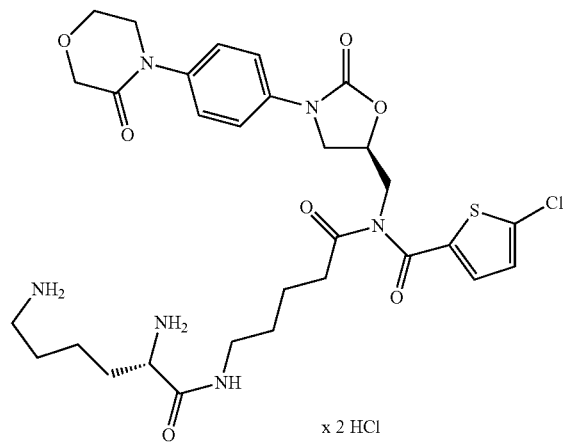 [SMILES: NCCCC[C@H](N)C(=O)NCCCCC(=O)N(C[C@H]1CN(c2ccc(N3CCOCC3=O)cc2)C(=O)O1)C(=O)c1ccc(Cl)s1 ; "x 2 HCl"]

x 2 HCl

Stage a):

39 mg (87 µmol) of 2,5-dioxopyrrolidin-1-yl-$N^2$,$N^6$-bis(tert-butoxycarbonyl)-L-lysinate are dissolved together with 25 mg (44 µmol) of Example 4A in 40 ml of DMF, and then 350 µl of a 0.1M solution of ethyldiisopropylamine in DMF are added a little at a time. Stirring at RT for 10 min is followed by concentrating. The residue is taken up in ethyl acetate and extracted twice with 10% sodium carbonate solution. The organic phase is concentrated and the residue is purified by flash chromatography initially with ethyl acetate and then with toluene/ethanol 1:1 as eluent. The appropriate fractions which contain the still impure target compound are combined and concentrated in vacuo. The residue is then purified once more by preparative HPLC (method 1a). The appropriate fractions are concentrated and dried under high vacuum to obtain 5 mg (11% of theory) of the protected title compound.

HPLC (method 2): $R_t$=5.27 min

LC-MS (method 3): $R_t$=2.59 min; m/z=863 (M+H)$^+$.

Stage b):

5 mg of the protected example are taken up in 2.5 ml of anhydrous trifluoroacetic acid and stirred at RT for 20 min. The batch is then concentrated in vacuo at 25° C. or below and the residue is subsequently taken up in hydrochloric acid (pH 3) and extracted twice with dichloromethane. The aqueous phase is separated off and lyophilized to obtain 3.8 mg (89% of theory) of the title compound.

HPLC (method 2): $R_t$=4.12 min;

LC-MS (method 3): $R_t$=1.02 min; m/z=663 (M+H)$^+$.

$^1$H NMR (500 MHz, DMSO-d$_6$): δ=1.3 (m, 2H), 1.4 (m, 2H), 1.5-1.6 (m, 4H), 1.7 (m, 2H), 2.55 (m, 2H), 2.75 (m, 2H), 3.1 (m, 2H), 3.7 (t, 2H), 3.8 (dd, 1H), 3.95 (t, 2H), 4.1-4.3 (m, 6H), 4.9 (m, 1H), 7.3 (d, 1H), 7.4 (d, 2H), 7.5 (d, 2H), 7.6 (d, 1H), 7.85 (m, 3H), 8.15 (m, 3H), 8.45 (t, 1H).

Example 15

5-Chloro-N-({(5S)-2-oxo-3-[4-(3-oxomorpholin-4-yl)phenyl]-1,3-oxazolidin-5-yl}methyl)-N-[5-(L-threonylamino)pentanoyl]thiophene-2-carboxamide hydrochloride

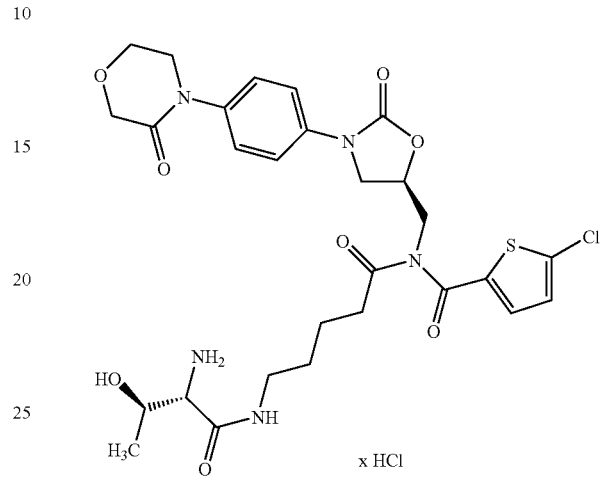

x HCl

Stage a):

277 mg (875 µmol) of 2,5-dioxopyrrolidin-1-yl N(tert-butoxycarbonyl)-L-threoninate are initially charged together with 13.7 µl of ethyldiisopropylamine in 1 ml of DMF. 50 mg (87 µmol) of the compound of Example 4A dissolved in 5 ml of DMF are added dropwise over a period of 1 h. Stirring at RT for 30 min is followed by concentrating and the residue is purified by flash chromatography initially with ethyl acetate and later with toluene/ethanol 1:1 as eluent. The appropriate fractions which contain impure target compound are combined and concentrated in vacuo. The residue is then purified once more by preparative HPLC (method 1a). The appropriate fractions are concentrated and dried under high vacuum to obtain 22 mg (34% of theory) of the protected title compound.

HPLC (method 2a): $R_t$=4.8 min

LC-MS (method 12): $R_t$=3.13 min; m/z=736 (M+H)$^+$.

Stage b):

22 mg (30 µmol) of the protected compound are taken up in 5 ml of anhydrous trifluoroacetic acid and stirred at RT for 20 min. The batch is then concentrated in vacuo at 25° C. or below and the residue is subsequently taken up in 30 ml of hydrochloric acid (pH 3) and extracted twice with 30 ml of dichloromethane and once with 30 ml of ethyl acetate. The aqueous phase is separated off and lyophilized to obtain 15 mg (75% of theory) of the title compound.

HPLC (method 2): $R_t$=4.2 min;

LC-MS (method 3): $R_t$=1.39 min; m/z=636 (M+H)$^+$.

$^1$H NMR (500 MHz, DMSO-d$_6$): δ=1.1 (d, 3H), 1.4 (m, 2H), 1.6 (m, 2H), 2.6 (t, 2H), 3.0 and 3.15 (2m, 2H), 3.4 (m, 1H), 3.7 (t, 2H), 3.8 (m, 2H), 3.95 (t, 2H), 4.1-4.3 (m, 5H), 4.95 (m, 1H), 5.5 (d, 1H), 7.3 (d, 1H), 7.4 (d, 2H), 7.5 (d, 2H), 7.6 (d, 1H), 8.05 (m, 3H), 8.4 (t, 1H).

Example 16

N-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)-L-tyrosinamide hydrochloride

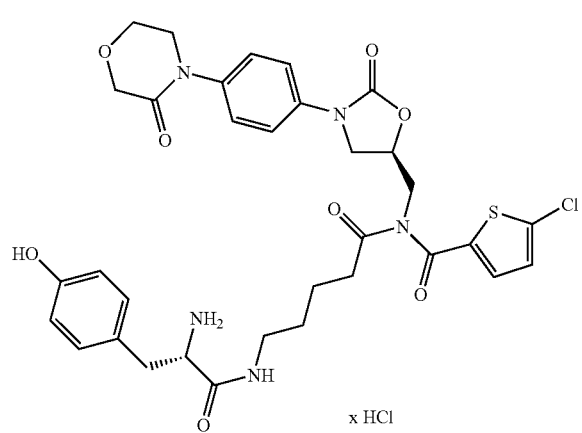 [SMILES: N[C@@H](Cc1ccc(O)cc1)C(=O)NCCCCC(=O)N(C[C@H]1CN(c2ccc(N3CCOCC3=O)cc2)C(=O)O1)C(=O)c1ccc(Cl)s1 ; "x HCl"]

Stage a):

331 mg (875 μmol) of 2,5-dioxopyrrolidin-1-yl N-(tert-butoxycarbonyl)-L-tyrosinate are initially charged together with 13.7 μl of ethyldiisopropylamine in 1 ml of DMF. 50 mg (87 μmol) of the compound of Example 4A dissolved in 5 ml of DMF are added dropwise over a period of 1 h. Stirring at RT for 30 min is followed by concentrating and the residue is purified by flash chromatography initially with ethyl acetate and later with toluene/ethanol 1:1 as eluent. The appropriate fractions which contain impure target compound are combined and concentrated in vacuo. The residue is then purified once more by preparative HPLC (method 1a). The appropriate fractions are concentrated and dried under high vacuum to obtain 26 mg (37% of theory) of the protected title compound.

HPLC (method 2a): $R_t$=5.0 min

LC-MS (method 3): $R_t$=2.38 min; m/z=798 (M+H)$^+$.

Stage b):

26 mg (33 μmol) of the protected compound are taken up in 5 ml of anhydrous trifluoroacetic acid and stirred at RT for 10 min. The batch is then concentrated in vacuo at 25° C. or below and the residue is subsequently taken up in 60 ml of hydrochloric acid (pH 3). Undissolved fractions are filtered off. The aqueous phase is then lyophilized to obtain 23 mg (96% of theory) of the title compound.

HPLC (method 2): $R_t$=4.4 min;

LC-MS (method 12): $R_t$=2.09 min; m/z=698 (M+H)$^+$.

$^1$H NMR (500 MHz, DMSO-d$_6$): δ=1.3 (m, 2H), 1.5 (m, 2H), 2.8-3.2 (m, 4H), 3.7 (t, 2H), 3.8 (m, 2H), 3.95 (t, 2H), 4.1-4.3 (m, 5H), 4.9 (m, 1H), 6.7 (d, 2H), 7.0 (d, 2H), 7.3 (d, 1H), 7.4 (d, 2H), 7.5 (d, 2H), 7.65 (d, 1H), 8.1 (m, 3H), 8.3 (t, 1H), 9.4 (s, 1H).

Example 17

N$^1$-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)-L-aspartamide hydrochloride

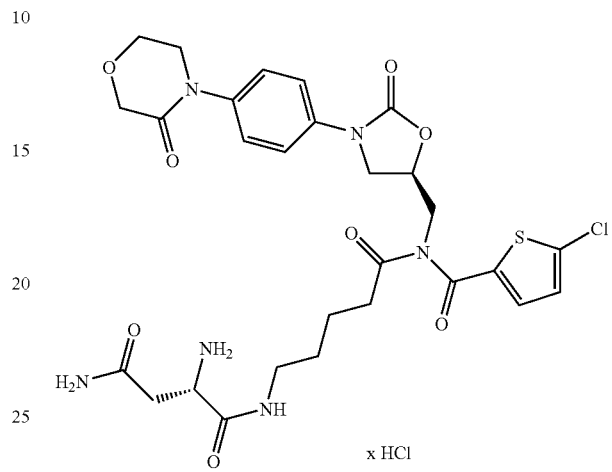

Stage a):

288 mg (875 μmol) of 2,5-dioxopyrrolidin-1-yl N$^2$-(tert-butoxycarbonyl)-L-asparaginate are initially charged together with 13.7 μl of ethyldiisopropylamine in 1 ml of DMF. 50 mg (87 μmol) of the compound of Example 4A dissolved in 5 ml of DMF are added dropwise over a period of 30 min. Stirring at RT for a further 30 min is followed by concentrating and the residue is purified by preparative HPLC (method 1a). The appropriate fractions which still contain a little compound (A) as an impurity are concentrated and dried under high vacuum to obtain 29 mg of crude product of the protected title compound, which are used in the next stage without further purification.

HPLC (method 2): $R_t$=4.5 min

LC-MS (method 3): $R_t$=2.07 min; m/z=749 (M+H)$^+$.

Stage b):

26 mg of the protected crude product from stage a) are taken up in 5 ml of anhydrous trifluoroacetic acid and stirred at RT for 10 min. The batch is then concentrated in vacuo at 25° C. or below and the residue is subsequently taken up in 50 ml of hydrochloric acid (pH 3). Undissolved fractions are filtered off and the aqueous phase is concentrated. The residue is then purified by preparative HPLC (method 1a). The appropriate fractions are concentrated and dried under high vacuum. The residue is then lyophilized from hydrochloric acid which has been adjusted to pH 3, to obtain 14 mg (53% of theory) of the title compound.

HPLC (method 2a): $R_t$=4.1 min;

LC-MS (method 12): $R_t$=1.84 min; m/z=649 (M+H)$^+$.

$^1$H NMR (500 MHz, DMSO-d$_6$): δ=1.4 (m, 2H), 1.55 (m, 2H), 2.55 (m, 2H), 2.65 (m, 2H), 3.0-3.1 (m, 2H), 3.7 (t, 2H), 3.8 (dd, 1H), 3.95 (m, 3H), 4.1-4.3 (m, 5H), 4.9 (m, 1H), 7.2 (s, 1H), 7.3 (d, 1H), 7.4 (d, 2H), 7.5 (d, 2H), 7.6 (m, 2H), 8.0 (m, 3H), 8.3 (t, 1H).

Example 18

N-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)-L-phenylalaninamide hydrochloride

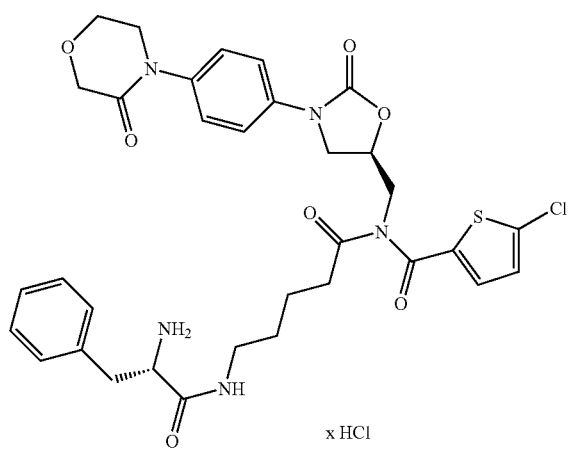 [SMILES: N[C@@H](Cc1ccccc1)C(=O)NCCCCC(=O)N(C[C@H]1CN(c2ccc(N3CCOCC3=O)cc2)C(=O)O1)C(=O)c1ccc(Cl)s1 ; "x HCl"]

Stage a):

317 mg (875 μmol) of 2,5-dioxopyrrolidin-1-yl N-(tert-butoxycarbonyl)-L-phenylalaninate are initially charged together with 13.7 μl of ethyldiisopropylamine in 1 ml of DMF. 50 mg (87 μmol) of the compound of Example 4A dissolved in 5 ml of DMF are added dropwise over a period of 30 min. Stirring at RT for 30 min is followed by concentrating. The residue is eluted by flash chromatography initially with dichloromethane/ethyl acetate eluents in a ratio of 3:1, 2:1 and 1:1. This is followed by elution with pure ethyl acetate and finally with ethanol as eluent. The corresponding fractions which contain still impure target compound are purified and concentrated in vacuo. The residue is then purified once more by preparative HPLC (method 1a). The appropriate fractions are concentrated and dried under high vacuum to obtain 34 mg (50% of theory) of the protected title compound.

HPLC (method 2a): $R_t$=5.34 min

LC-MS (method 12): $R_t$=3.47 min; m/z=782 (M+H)$^+$.

Stage b):

33 mg (42 μmol) of the protected compound are dissolved in dichloromethane and admixed with 1.5 ml of anhydrous trifluoroacetic acid and stirred at RT for 10 min. The batch is then concentrated in vacuo at 25° C. or below and the residue is subsequently taken up in 5 ml of hydrochloric acid (pH 3). The aqueous phase is then lyophilized to obtain 28 mg (93% of theory) of the title compound.

HPLC (method 2): $R_t$=4.5 min;

LC-MS (method 12): $R_t$=2.08 min; m/z=682 (M+H)$^+$.

$^1$H NMR (400 MHz, DMSO-d$_6$): δ=1.25 (m, 2H), 1.5 (m, 2H), 2.9-3.2 (m, 4H), 3.7 (m, 2H), 3.8 (t, 2H), 3.9 (m, 1H), 4.0 (t, 2H), 4.1-4.3 (m, 5H), 4.9 (m, 1H), 7.2 (d, 2H), 7.2-7.35 (m, 4H), 7.4 (d, 2H), 7.5 (d, 2H), 7.65 (d, 1H), 8.2 (m, 2H), 8.3 (t, 1H).

Example 19

N$^1$-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)-L-glutamamide hydrochloride

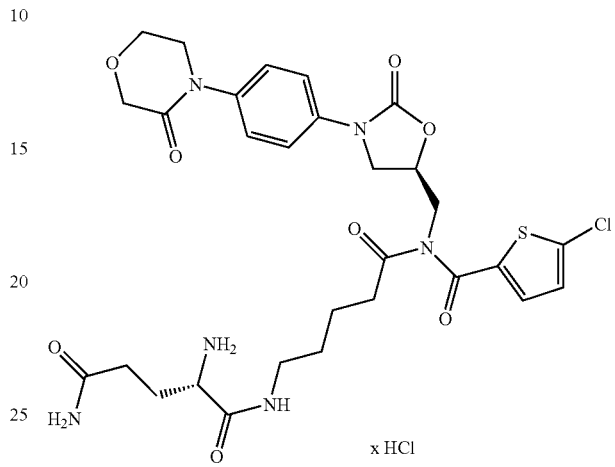

Stage a):

300 mg (875 μmol) of 2,5-dioxopyrrolidin-1-yl N$^2$-(tert-butoxycarbonyl)-L-glutaminate are initially charged together with 13.7 μl of ethyldiisopropylamine in 1 ml of DMF. 50 mg (87 μmol) of the compound of Example 4A dissolved in 5 ml of DMF are added dropwise over a period of 30 min. Stirring at RT for 30 min is followed by concentrating and the residue is purified by flash chromatography with dichloromethane/ethyl acetate/methanol initially in a ratio of 150:50:5, then in a ratio of 150:50:10 and finally in a ratio of 150:50:20 as eluent. The appropriate fractions which contain still impure target compound are combined and concentrated in vacuo. The residue is then purified once more by preparative HPLC (method 1a). The appropriate fractions are concentrated and dried under high vacuum to obtain 24 mg (34% of theory) of the protected title compound.

HPLC (method 2a): $R_t$=4.57 min

LC-MS (method 12): $R_t$=2.97 min; m/z=763 (M+H)$^+$.

Stage b):

24 mg (35 μmol) of the protected compound are dissolved in dichloromethane and admixed with 2 ml of anhydrous trifluoroacetic acid and stirred at RT for 10 min. The batch is then concentrated in vacuo at 25° C. or below and the residue is subsequently taken up in 15 ml of hydrochloric acid (pH 3). The batch is initially extracted twice with dichloromethane and then once with ethyl acetate. The aqueous phase is then lyophilized to obtain 14 mg (59% of theory) of the title compound.

LC-MS (method 12): $R_t$=1.60 min; m/z=663 (M+H)$^+$.

$^1$H NMR (400 MHz, DMSO-d$_6$): δ=1.4 (m, 2H), 1.6 (m, 2H), 1.9 (q, 2H), 2.15 (m, 2H), 2.55 (m, 2H), 3.1 (m, 2H), 3.7 (t, 2H), 3.8 (dd, 1H), 4.0 (t, 2H), 4.1-4.3 (m, 5H), 4.9 (m, 1H), 6.9 (s, 1H), 7.3 (d, 1H), 7.4 (m, 3H), 7.5 (d, 2H), 7.65 (d, 1H), 8.1 (m, 3H), 8.4 (t, 1H).

Example 20

N-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)-L-alpha-glutamine hydrochloride

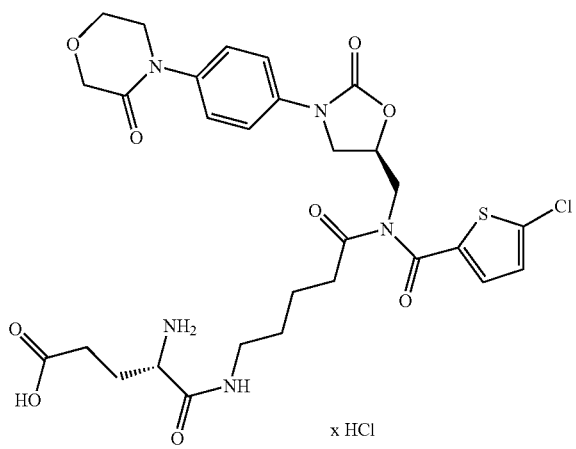 [SMILES: N[C@@H](CCC(=O)O)C(=O)NCCCCC(=O)N(C[C@H]1CN(c2ccc(N3CCOCC3=O)cc2)C(=O)O1)C(=O)c1ccc(Cl)s1 ; "x HCl"]

Stage a):

350 mg (875 µmol) of 5-tert-butyl 1-(2,5-dioxopyrrolidin-1-yl)-N-(tert-butoxycarbonyl)-L-glutamate are initially charged together with 13.7 µl of ethyldiisopropylamine in 1 ml of DMF. 50 mg (87 µmol) of the compound of Example 4A dissolved in 5 ml of DMF are added dropwise over a period of 30 min. Stirring at RT for 30 min is followed by concentrating and the residue is purified by flash chromatography with dichloromethane/ethyl acetate/methanol initially in a ratio of 150:50:5, then in a ratio of 150:50:10 and finally in a ratio of 150:50:20 as eluent. The appropriate fractions which contain still impure target compound are combined and concentrated in vacuo. The residue is then purified once more by preparative HPLC (method 1a). The appropriate fractions are concentrated and dried under high vacuum to obtain 35 mg (49% of theory) of the protected title compound.

HPLC (method 2a): $R_t$=5.4 min

LC-MS (method 3): $R_t$=2.63 min; m/z=820 (M+H)$^+$.

Stage b):

35 mg (43 µmol) of the protected compound are dissolved in dichloromethane and admixed with 1.5 ml of anhydrous trifluoroacetic acid and stirred at RT for 2 h. The batch is then concentrated in vacuo at 25° C. or below and the residue is subsequently taken up in 10 ml of hydrochloric acid (pH 3) and lyophilized to obtain 29 mg (97% of theory) of the title compound.

LC-MS (method 12): $R_t$=1.72 min; m/z=664 (M+H)$^+$.

$^1$H NMR (400 MHz, DMSO-d$_6$): δ=1.4 (m, 2H), 1.6 (m, 2H), 1.9 (q, 2H), 2.3 (m, 2H), 2.55 (m, 2H), 3.1 (m, 2H), 3.7 (t, 2H), 3.8 (dd, 1H), 4.0 (t, 2H), 4.1-4.3 (m, 5H), 4.9 (m, 1H), 7.3 (d, 1H), 7.4 (d, 2H), 7.5 (d, 2H), 7.6 (d, 1H), 8.1 (m, 3H), 8.45 (t, 1H).

Example 21

5-Chloro-N-({(5S)-2-oxo-3-[4-(3-oxomorpholin-4-yl)phenyl]-1,3-oxazolidin-5-yl}methyl)-N-[5-(L-serylamino)pentanoyl]thiophene-2-carboxamide hydrochloride

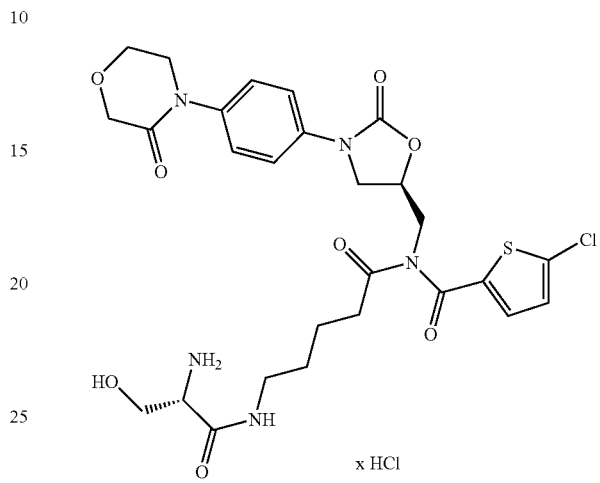

Stage a):

350 mg (875 µmol) of 2,5-dioxopyrrolidin-1-yl N-(tert-butoxycarbonyl)-L-serinate are initially charged together with 13.7 µl of ethyldiisopropylamine in 1 ml of DMF. 50 mg (87 µmol) of the compound of Example 4A dissolved in 5 ml of DMF are added dropwise over a period of 30 min. Stirring at RT for 30 min is followed by concentrating and the residue is purified by flash chromatography initially with dichloromethane/ethyl acetate 3:1 and then dichloromethane/ethyl acetate/methanol in a ratio of 150:50:5, then in a ratio of 150:50:10 and finally in a ratio of 150:50:20 as eluent. The appropriate fractions which contain still impure target compound are combined and concentrated in vacuo. The residue is then purified once more by preparative HPLC (method 1a). The appropriate fractions are concentrated and dried under high vacuum to obtain 33 mg (52% of theory) of the protected title compound.

LC-MS (method 12): $R_t$=2.87 min; m/z=722 (M+H)$^+$.

Stage b):

33 mg (46 µmol) of the protected compound are dissolved in dichloromethane and admixed with 1.6 ml of anhydrous trifluoroacetic acid and stirred at RT for 10 min. The batch is then concentrated in vacuo at 25° C. or below and the residue is subsequently taken up in 5 ml of hydrochloric acid (pH 3) and lyophilized to obtain 24 mg (80% of theory) of the title compound.

LC-MS (method 12): $R_t$=1.81 min; m/z=622 (M+H)$^+$.

$^1$H NMR (400 MHz, DMSO-d$_6$): δ=1.4 (m, 2H), 1.6 (m, 2H), 2.55 (m, 2H), 3.1 (dt, 2H), 3.6-3.8 (m, 5H), 3.85 (dd, 1H), 4.1-4.3 (m, 5H), 4.95 (m, 1H), 5.4 (m, 1H), 7.3 (d, 1H), 7.4 (d, 2H), 7.5 (d, 2H), 7.6 (d, 1H), 8.1 (m, 3H), 8.4 (t, 1H).

Example 22

N-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)-L-leucinamide hydrochloride

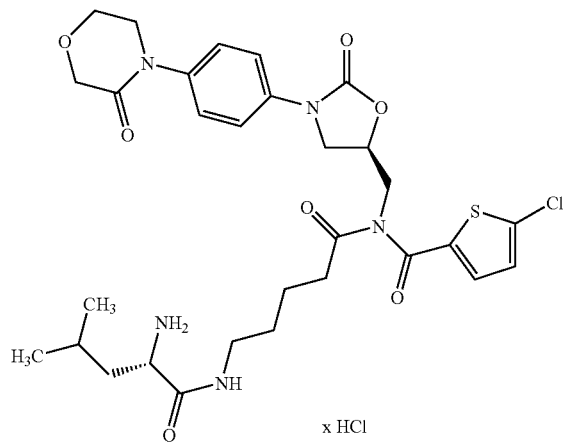 [SMILES: CC(C)C[C@H](N)C(=O)NCCCCC(=O)N(C[C@H]1CN(c2ccc(N3CCOCC3=O)cc2)C(=O)O1)C(=O)c1ccc(Cl)s1 ; "x HCl"]

Stage a):

287 mg (875 μmol) of 2,5-dioxopyrrolidin-1-yl N-(tert-butoxycarbonyl)-L-leucinate are initially charged together with 13.7 μl of ethyldiisopropylamine in 1 ml of DMF. 50 mg (87 μmol) of the compound of Example 4A dissolved in 5 ml of DMF are added dropwise over a period of 30 min. Stirring at RT for 30 min is followed by concentrating and the residue is purified by flash chromatography initially with dichloromethane/ethyl acetate 3:1 and then dichloromethane/ethyl acetate/methanol in a ratio of 150:50:5, then in a ratio of 150:50:10 and finally in a ratio of 150:50:20 as eluent. The appropriate fractions which contain still impure target compound are combined and concentrated in vacuo. The residue is then purified once more by preparative HPLC (method 1a). The appropriate fractions are concentrated and dried under high vacuum to obtain 10 mg (15% of theory) of the protected title compound.

LC-MS (method 12): $R_t$=3.44 min; m/z=748 (M+H)$^+$.

Stage b):

10.2 mg (14 μmol) of the protected compound are dissolved in dichloromethane and admixed with 0.5 ml of anhydrous trifluoroacetic acid and stirred at RT for 15 min. The batch is then concentrated in vacuo at 25° C. or below and the residue is subsequently taken up in 5 ml of dilute hydrochloric acid (pH 3) and lyophilized to obtain 7 mg (73% of theory) of the title compound.

LC-MS (method 12): $R_t$=2.25 min; m/z=648 (M+H)$^+$.

Example 23

N-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxobutyl)-L-histidinamide hydrochloride

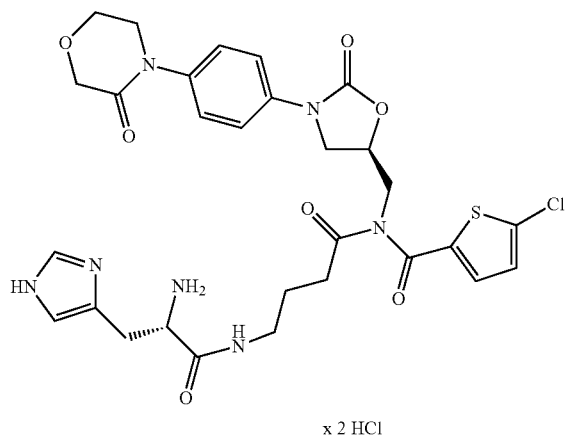 [SMILES: N[C@@H](Cc1c[nH]cn1)C(=O)NCCCC(=O)N(C[C@H]1CN(c2ccc(N3CCOCC3=O)cc2)C(=O)O1)C(=O)c1ccc(Cl)s1 ; "x 2 HCl"]

Stage a):

195 mg (431 μmol) of 2,5-dioxopyrrolidin-1-yl N,1-bis(tert-butoxycarbonyl)-L-histidinate are initially charged together with 645 μl of a 0.1M solution of ethyldiisopropylamine in DMF in 3 ml of DMF. 40 mg (72 μmol) of Example 3A dissolved in 17 ml of DMF are added dropwise over a period of 1 h. Stirring at RT for 30 min is followed by concentrating and the residue is purified by flash chromatography initially with acetonitrile and then with acetonitrile/water 10:1 as eluent. The appropriate fractions which contain still impure target compound are combined and concentrated in vacuo. The residue is then purified once more by preparative HPLC (method 1a). The appropriate fractions which contain a mixture of the bis-Boc-protected example and the mono-Boc-protected example are concentrated and dried under high vacuum to obtain 30 mg (55% of theory) of a mixture of the mono- and bis-Boc-protected title compound.

HPLC (method 2): $R_t$=4.47 min; 4.91 min

LC-MS (method 3): $R_t$=1.53 min; m/z=758 (M+H)$^+$; $R_t$=2.45 min; m/z=858 (M+H)$^+$.

Stage b):

30 mg of the mixture of the bis-Boc-protected intermediate and the mono-Boc-protected intermediate are taken up in 2 ml of anhydrous trifluoroacetic acid and stirred at RT for 10 min. Then the batch is concentrated in vacuo at 25° C. or below and the residue is subsequently lyophilized twice from hydrochloric acid pH 3 to obtain 24 mg (83% of theory) of the title compound.

HPLC (method 2): $R_t$=4.07 min;

LC-MS (method 13): $R_t$=2.41 min; m/z=658 (M+H)$^+$.

Example 24

N-(5-{[(5-Chloro-2-thienyl)carbonyl]({(5S)-2-oxo-3-[4-(3-oxomorpholin-4-yl)phenyl]-1,3-oxazolidin-5-yl}methyl)amino}-5-oxopentyl)-L-alpha-asparagine hydrochloride

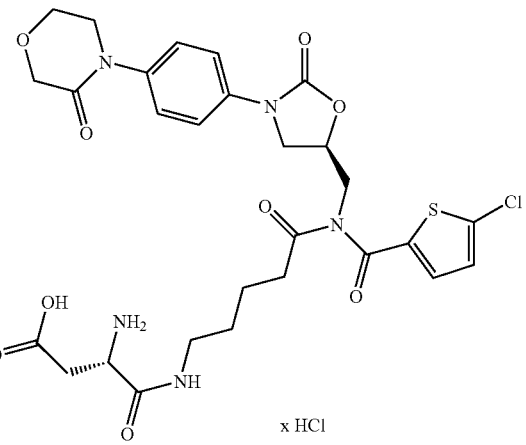

Stage a):

338 mg (875 μmol) of 5-tert-butyl 1-(2,5-dioxopyrrolidin-1-yl)-N-(tert-butoxycarbonyl)-L-aspartate are initially charged together with 13.7 μl of ethyldiisopropylamine in 1 ml of DMF. 50 mg (87 μmol) of the compound of Example 4A dissolved in 5 ml of DMF are added dropwise over a period of 30 min. Stirring at RT for 30 min is followed by concentrating and the residue is purified by flash chromatography initially with dichloromethane/ethyl acetate 3:1 and then dichloromethane/ethyl acetate/methanol in a ratio of 150:50:5, then in a ratio of 150:50:10 and finally in a ratio of 150:50:20 as eluent. The appropriate fractions which contain still impure target compound are combined and concentrated in vacuo. The residue is then purified once more by preparative HPLC (method 1a). The appropriate fractions are concentrated and dried under high vacuum to obtain 36 mg (51% of theory) of the protected title compound.

HPLC (method 2a): $R_t$=5.4 min

LC-MS (method 12): $R_t$=3.52 min; m/z=806 (M+H)$^+$.

Stage b):

36 mg (45 µmol) of the protected compound are dissolved in dichloromethane and admixed with 1.5 ml of anhydrous trifluoroacetic acid and stirred at RT for 2 h. The batch is then concentrated in vacuo at 25° C. or below and the residue is subsequently taken up in 5 ml of hydrochloric acid (pH 3) and lyophilized to obtain 28 mg (91% of theory) of the title compound.

$^1$H NMR (400 MHz, DMSO-d$_6$): δ=1.4 (m, 2H), 1.6 (m, 2H), 2.7-2.9 (m, 4H), 3.1 (m, 2H), 3.7 (t, 2H), 3.8 (dd, 1H), 4.0 (t, 2H), 4.1-4.3 (m, 5H), 4.9 (m, 1H), 7.3 (d, 1H), 7.4 (d, 2H), 7.5 (d, 2H), 7.6 (d, 1H), 8.2 (m, 3H), 8.4 (t, 1H), 13.0 (m, 1H).

B. DETERMINATION OF SOLUBILITY, STABILITY AND LIBERATION BEHAVIOUR a) Determination of the Solubility:

The test substance is suspended in water or dilute hydrochloric acid (pH 4). This suspension is shaken at room temperature for 24 h. After ultracentrifugation at 224 000 g for 30 min, the supernatant is diluted with DMSO and analysed by HPLC. A two-point calibration plot of the test compound in DMSO is used for quantification.

HPLC Method:

Agilent 1100 with DAD (G1315A), quat. pump (G1311A), autosampler CTC HTS PAL, degasser (G1322A) and column thermostat (G1316A); column: Kromasil C18, 60×2.1 mm, 3.5 µm; temperature: 30° C.; eluent A: water+5 ml of perchloric acid/liter, eluent B: acetonitrile; flow rate: 0.7 ml/min; gradient: 0-0.5 min 98% A, 2% B; ramp 0.5-4.5 min 10% A, 90% B; 4.5-6 min 10% A, 90% B; ramp 6.5-6.7 min 98% A, 2% B; 6.7-7.5 min 98% A, 2% B.

The solubilities of representative exemplary embodiments in dilute hydrochloric acid (pH 4) are shown in Table 1:

TABLE 1

| Example No. | Solubility [mg/litre] |
| --- | --- |
| 3 | >3500 |
| 7 | >500 |
| 12 | >3000 |
| 14 | 1900 |

No decomposition of the exemplary compounds in these solutions is observed.

The solubility of the underlying active substance [compound (A)] in dilute hydrochloric acid (pH 4) is determined in this test to be 8.1 mg/liter.

b) Stability in Buffer at Various pH Values:

0.3 mg of the test substance is weighed into a 2 ml HPLC vial and 0.5 ml of acetonitrile is added. The substance is dissolved by putting the sample vessel in an ultrasonic bath for about 10 seconds. Then 0.5 ml of the respective buffer solution is added, and the sample is again treated in the ultrasonic bath.

Buffer solutions employed:

pH 4.0: 1 liter of Millipore water is adjusted to pH 4.0 with 1 N hydrochloric acid;

pH 7.4: 90 g of sodium chloride, 13.61 g of potassium dihydrogen phosphate and 83.35 g of 1 M sodium hydroxide solution are made up to 1 liter with Millipore water and then diluted 1:10.

5 µl portions of the test solution are analysed by HPLC for their content of unchanged test substance every hour over a period of 24 hours at 25° C. The percentage areas of the appropriate peaks are used for quantification.

HPLC Method:

Agilent 1100 with DAD (G1314A), binary pump (G1312A), autosampler (G1329A), column oven (G1316A), thermostat (G1330A); column: Kromasil 100 C18, 60 mm×2.1 mm, 3.5 µm; column temperature: 30° C.; eluent A: water+5 ml of perchloric acid/liter, eluent B: acetonitrile; gradient: 0-1.0 min 98% A, 2% B→1.0-9.0 min 2% A, 98% B; 9.0-13.0 min 2% A, 98% B; 13.0-13.5 min 98% A, 2% B; 13.5-15.0 98% A, 2% B; flow rate: 0.75 ml/min; UV detection: 210 nm.

The ratios of the peak areas (F) at the respective time points in relation to the peak areas at the starting time are shown in Table 2 for representative exemplary embodiments:

TABLE 2

| Example No. | Buffer pH | % test substance after 4 h [F(t = 4 h) × 100/F(t = 0 h)] | % test substance after 24 h [F(t = 24 h) × 100/F(t = 0 h)] |
| --- | --- | --- | --- |
| 2 | 4 | 101 | 101 |
| 2 | 7.4 | 99 | 94 |
| 3 | 4 | 100 | 101 |
| 3 | 7.4 | 100 | 100 |
| 4 | 4 | 100 | 100 |
| 4 | 7.4 | 92 | 77 |
| 5 | 4 | 100 | 100 |
| 5 | 7.4 | 96 | 84 |
| 6 | 4 | 99 | 99 |
| 6 | 7.4 | 90 | 53 |
| 7 | 4 | 100 | 101 |
| 7 | 7.4 | 97 | 84 |
| 8 | 4 | 100 | 100 |
| 8 | 7.4 | 86 | 48 |
| 10 | 4 | 100 | 101 |
| 10 | 7.4 | 100 | 100 |
| 11 | 4 | 101 | 101 |
| 11 | 7.4 | 100 | 99 |
| 12 | 4 | 100 | 101 |
| 12 | 7.4 | 99 | 93 |
| 14 | 4 | 100 | 100 |
| 14 | 7.4 | 98 | 88 |

In this test there is found to be at pH 7.4 a simultaneous increase in the active ingredient compound (A) with the decrease in the content of test substance.

c) In Vitro Stability in Rat and Human Plasma *):

A defined plasma volume (e.g. 2.0 ml) is warmed to 37° C. in a closed test tube in a waterbath. After the intended temperature is reached, a defined amount of the test substance is added as solution (volume of the solvent not more than 2% of the plasma volume). The plasma is shaken and a first sample (50-100 µl) is immediately taken. Then 4-6 further aliquots are taken in the period up fo 2 h after the start of incubation.

Acetonitrile is added to the plasma samples to precipitate proteins. After centrifugation, the test substance and, where appropriate, known cleavage products of the test substance in the supernatant are determined quantitatively with a suitable LC/MS-MS method.

*) Determinations of stability in heparinized blood (rat or human blood) are carried out—as described for plasma.

d) Determination of the Metabolic Stability in Hepatocytes:

Metabolic stabilities of new test compounds in the presence of hepatocytes are determined by incubating the compounds at low concentrations (preferably below 1 µM) and with low cell counts (preferably with 1×10$^6$ cells/ml) in order to ensure as far as possible linear kinetic conditions in the experiment. Seven samples of the incubation solution are taken in a fixed time pattern for the LC-MS analysis in order to determine the half-life (the degradation) of the compound. Various clearance parameters (CL) (see below) and Fmax values are calculated from this half-life (see below).

The CL and Fmax values represent a measure of the 'phase 1' and 'phase 2' metabolism of the compound in the hepatocytes. In order to minimize the influence of the organic solvent on the enzymes in the incubation mixtures, these concentrations are generally limited to 1% (acetonitrile) or to 0.1% (DMSO).

A cell count for hepatocytes in the liver of $1.1 \times 10^8$ cells/g of liver is used for calculation for all species and breeds. CL parameters calculated on the basis of half-lives extending beyond the incubation time (normally 90 minutes) can be regarded only as rough guidelines.

The calculated parameters and their meaning are:
(QH=species–specific hepatic blood flow)
Fmax well-stirred [%] maximum possible bioavailability after oral administration
Calculation: $(1-CL_{blood} \text{ well-stirred}/QH) \ast 100$
$CL_{blood}$ well-stirred [L/(h*kg)] calculated blood clearance (well-stirred model)
Calculation: $(QH \ast CL'_{intrinsic})/(QH+CL'_{intrinsic})$
$CL'_{intrinsic}$ [ml/(min*kg)] maximum ability of the liver (of the hepatocytes) to metabolize a compound, on the assumption that the hepatic blood flow is not rate-limiting)
Calculation: $CL'_{intrinsic, apparent} \times$ species–specific hepatocyte count [$1.1 \times 10^8$/g of liver]×species–specific liver weight [g/kg]
$CL'_{intrinsic, apparent}$ [ml/(min*mg)] 'normalize' the elimination constant by dividing it by the cell count of hepatocytes employed x ($x \ast 10^6$/ml)
Calculation: $k_{el}$ [1/min]/(cell count [$x \ast 10^6$]/incubation volume [ml])

e) i.v. Pharmacokinetics in Wistar Rats:

On the day before administration of the substance, a catheter for obtaining blood is implanted in the jugular vein of the experimental animals (male Wistar rats, body weight 200-250 g) under Isofluran® anaesthesiat.

On the day of the experiment, a defined dose of the test substance is administered as solution into the tail vein using a Hamilton® glass syringe (bolus administration, duration of administration <10 s). Blood samples (8-12 time points) are taken through the catheter sequentially over the course of 24 h after administration of the substance. Plasma is obtained by centrifuging the samples in heparinized tubes. Acetonitrile is added to a defined plasma volume per time point to precipitate proteins. After centrifugation, test substance and, where appropriate, known cleavage products of the test substance in the supernatant are determined quantitatively using a suitable LC/MS-MS method.

The measured plasma concentrations are used to calculate pharmacokinetic parameters of the test substance and of the active ingredient compound (A) liberated therefrom, such as AUC, $C_{max}$, $T_{1/2}$ (half-life) and CL (clearance).

f) Determination of the Antithrombotic Effect in an Arteriovenous Shunt Model in Rats:

Fasting male rats (strain: HSD CPB:WU) are anaesthetized by intraperitoneal administration of a Rompun/Ketavet solution (12 mg/kg/50 mg/kg). Thrombus formation is induced in an arteriovenous shunt based on the method described by P. C. Wong et al. [*Thrombosis Research* 83 (2), 117-126 (1996)]. For this purpose, the left jugular vein and the right carotid artery are exposed. An 8 cm-long polyethylene catheter (PE60, from Becton-Dickinson) is secured in the artery, followed by a 6 cm-long Tygon tube (R-3606, ID 3.2 mm, from Kronlab) which contains a roughened nylon loop (60×0.26 mm, from Berkley Trilene) made into a double loop to produce a thrombogenic surface. A 2 cm-long polyethylene catheter (PE60, from Becton-Dickinson) is secured in the jugular vein and connected by a 6 cm-long polyethylene catheter (PE160, from Becton-Dickinson) to the Tygon tube. The tubes are filled with physiological saline before the shunt is opened. The extracorporeal circulation is maintained for 15 min. The shunt is then removed and the nylon thread with the thrombus is immediately weighed. The empty weight of the nylon thread has been found before the start of the experiment. The test substance (as solution in physiological saline adjusted to pH 4 with 0.1 N hydrochloric acid) is administered as bolus injection before attaching the extracorporeal circulation.

C. EXEMPLARY EMBODIMENTS OF PHARMACEUTICAL COMPOSITIONS

The compounds according to the invention can be converted for example into pharmaceutical preparations in the following way:

i.v. Solution:

The compound according to the invention is dissolved in a concentration below the saturation solubility in a physiologically tolerated solvent (e.g. isotonic saline, 5% glucose solution and/or 30% PEG 400 solution, each of which is adjusted to a pH of 3-5). The solution is sterilized by filtration where appropriate and/or dispensed into sterile and pyrogen-free injection containers.

The invention claimed is:
1. A compound of the formula

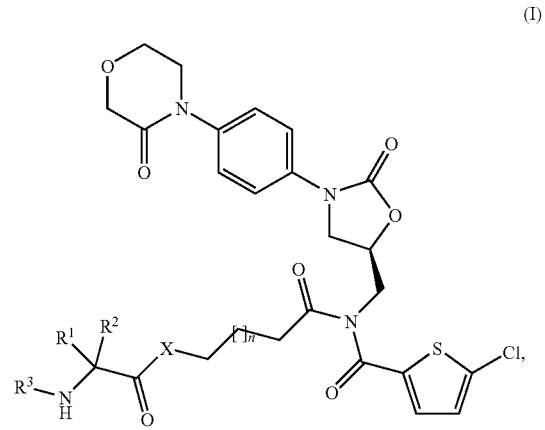

in which
n is 1 or 2,
X is an oxygen atom, a sulphur atom or NH,
$R^1$ is the side group of a natural a-amino acid or of its homologs or isomers,
$R^2$ is hydrogen or methyl,
$R^3$ is hydrogen,
or
$R^1$ and $R^2$ are linked via a $(CH_2)_3$ or $(CH_2)_4$ group and combine with the nitrogen or carbon atom to which they are attached to form a 5- or 6-membered ring, respectively, and salts thereof.
2. The compound of claim 1, in which
n is 1 or 2,
X is an oxygen atom, a sulphur atom or NH,
$R^1$ is hydrogen, methyl, propan-2-yl, propan-1-yl, 2-methylpropan-1-yl, imidazol-4-yl-methyl, hydroxymethyl, 1-hydroxyethyl, carboxymethyl, 2-carboxyethyl, carbamoylmethyl, 2-carbamoylethyl, 4-aminobutan-1-yl, 3-aminopropan-1-yl, 3-guanidinopropan-1-yl, benzyl or 4-hydroxybenzyl, R² is hydrogen or methyl, and
R³ is hydrogen
or
R¹ and R³ are linked via a (CH₂)₃ or (CH₂)₄ group and combine with the nitrogen or carbon atom to which they are attached to form a 5- or 6-membered ring, respectively.

3. The compound of claim 1, in which
n is 1 or 2,
X is NH,
R¹ is hydrogen, methyl, propan-2-yl, 2-methylpropan-1-yl, imidazol-4-ylmethyl, hydroxymethyl, 1-hydroxyethyl, carboxymethyl, 2-carboxyethyl, carbamoylmethyl, 2-carbamoylethyl, 4-aminobutan-1-yl, benzyl or 4-hydroxybenzyl,
R² is hydrogen, and
R³ is hydrogen.

4. A process for preparing a compound of the formula (I) of claim 1, or salts thereof, comprising:

[A] converting a compound of the formula (A):

(A)

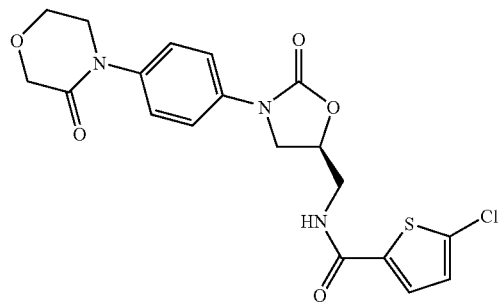

in an inert solvent in the presence of a base with a compound of the formula (II):

(II)

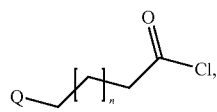

in which n has the meaning indicated in claim 1, and
Q is a leaving group,
into a compound of the formula (III):

(III)

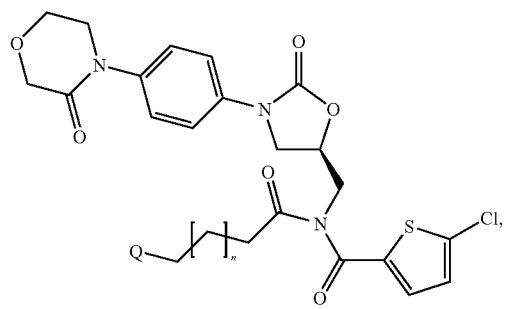

in which n has the meaning indicated in claim 1, and
Q has the meaning indicated in this claim,
reacting the compound of formula (III) according to process [A1] in an inert solvent with the caesium salt of an α-amino carboxylic acid or α-amino thiocarboxylic acid of the formula (IV)

(IV)

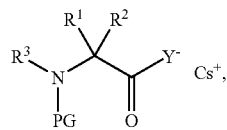

in which R¹, R² and R³ have the meaning indicated in claim 1,
PG is an amino protective group,
and
Y is O or S,
to give a compound of the formula (V)

(V)

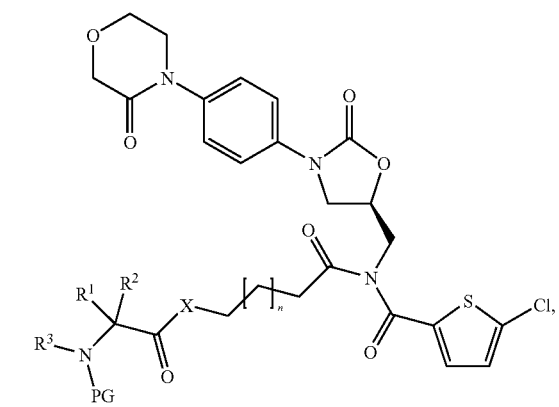

in which n, R¹, R² and R³ have the meaning indicated in claim 1,
PG has the meaning indicated in this claim, and
X is O or S,
and removing the protective group PG according to conventional methods to obtain a compound of the formula (I-A)

(I-A)

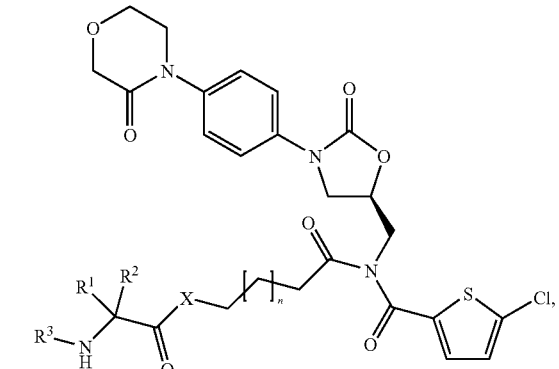

in which n, R¹, R² and R³ have the meaning indicated in claim 1, and
X is O or S, or
reacting the compound of formula (III) according to process [A2] in an inert solvent in the presence of a base with an a-amino thiocarboxylic acid of the formula (VI)

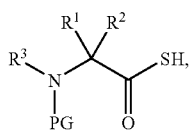

in which $R^1$, $R^2$ and $R^3$ have the meaning indicated in claim 1, and PG is an amino protective group, to give a compound of the formula (V-A)

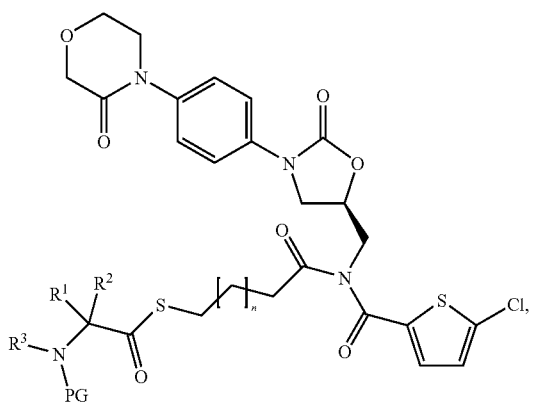

in which n, $R^1$, $R^2$ and $R^3$ have the meaning indicated in claim 1, and PG has the meaning indicated in this claim, and removing the protective group PG according to conventional methods to obtain a compound of the formula (I-A)

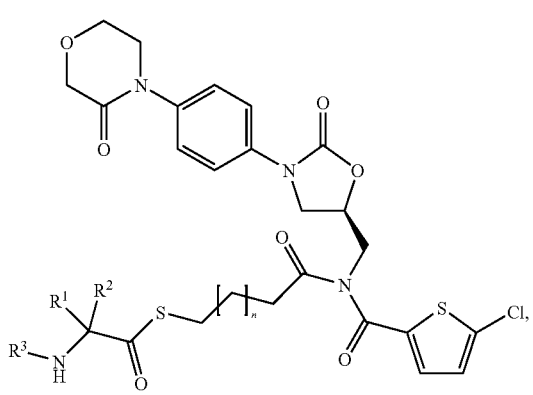

in which n, $R^1$, $R^2$ and $R^3$ have the meaning indicated in claim 1, or

[B] reacting compound (A) in an inert solvent in the presence of a base with a compound of the formula (VII)

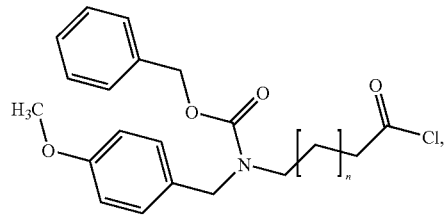

in which n has the meaning indicated in claim 1,
to give a compound of the formula (VIII)

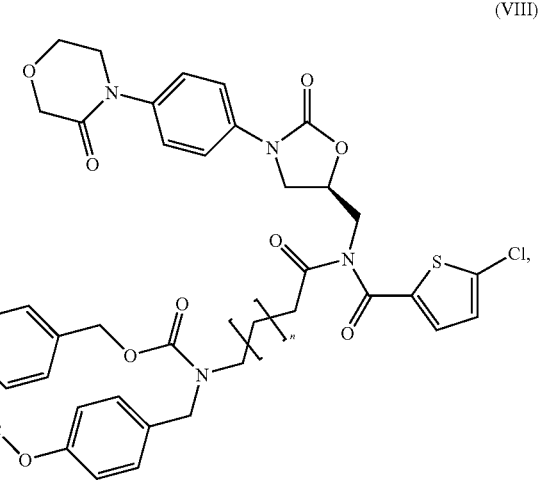

in which n has the meaning indicated in claim 1,
and removing the protective groups according to conventional methods to obtain a compound of the formula (IX):

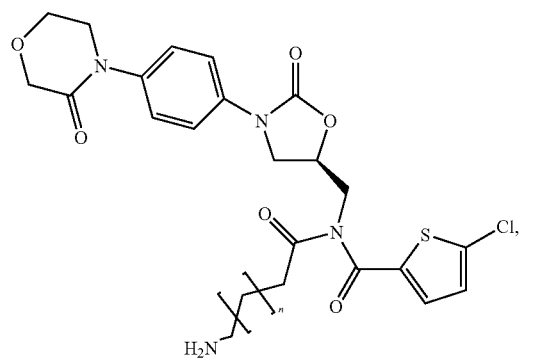

in which n has the meaning indicated in claim 1, and
combining the compound of formula (IX) in the presence of a base with a compound of the formula (X)

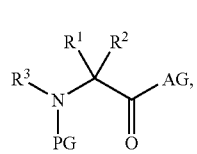

in which $R^1$, $R^2$ and $R^3$ have the meaning indicated in claim 1,

AG is hydroxyl or halogen, or with the carbonyl group of formula (X) forms an active ester, or a mixed anhydride, and PG is an amino protective group, to obtain a compound of the formula (XI)

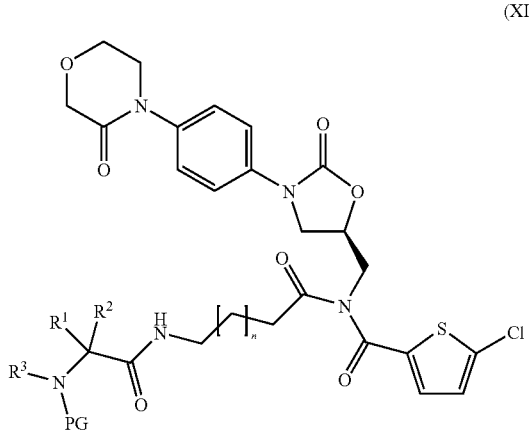
(XI)

in which n, $R^1$, $R^2$ and $R^3$ have the meaning indicated in claim 1, and PG has the meaning indicated in this claim, and removing the protective group PG from the compound of formula (XI) according to conventional methods to obtain a compound of the formula (I-B)

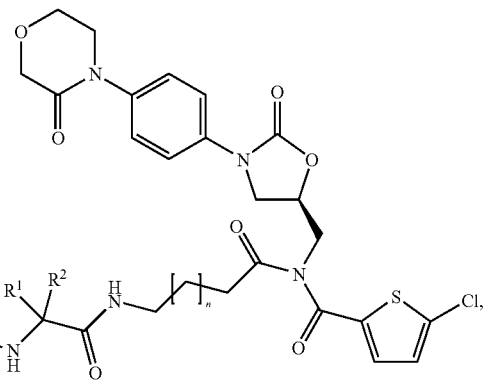
(I-B)

in which n, $R^1$, $R^2$ and $R^3$ have the meaning indicated in claim 1 and optionally converting the compounds of the formula (I-A) or (I-B) with the appropriate (i) solvents and/or (ii) acids into their salts.

5. A pharmaceutical composition comprising a compound of the formula (I) as defined in claim 1 and an inert, non-toxic, pharmaceutically suitable excipient.

* * * * *